(12) United States Patent
Gastaldo et al.

(10) Patent No.: US 8,817,249 B2
(45) Date of Patent: Aug. 26, 2014

(54) DEVICE AND METHOD FOR INSPECTING MOVING SEMICONDUCTOR WAFERS

(75) Inventors: Philippe Gastaldo, Pontcharra (FR); Frederic Pernot, Saint Egreve (FR); Olivier Piffard, Villard Bonnot (FR)

(73) Assignee: Alatech Semiconductor, Montbonnot-Saint Martin (FR)

( * ) Notice: Subject to any disclaimer, the term of this patent is extended or adjusted under 35 U.S.C. 154(b) by 121 days.

(21) Appl. No.: 13/696,322

(22) PCT Filed: May 4, 2011

(86) PCT No.: PCT/FR2011/000273
§ 371 (c)(1),
(2), (4) Date: Nov. 6, 2012

(87) PCT Pub. No.: WO2011/138524
PCT Pub. Date: Nov. 10, 2011

(65) Prior Publication Data
US 2013/0044316 A1      Feb. 21, 2013

(30) Foreign Application Priority Data
May 6, 2010   (FR) .................................. 10 01958

(51) Int. Cl.
*G01N 21/00* (2006.01)
*G01N 21/47* (2006.01)
*G01N 21/95* (2006.01)

(52) U.S. Cl.
CPC ............ *G01N 21/47* (2013.01); *G01N 21/9501* (2013.01); *G01N 21/9503* (2013.01)
USPC ................. 356/237.2; 356/237.1; 356/237.3; 356/237.4; 356/237.5

(58) Field of Classification Search
CPC    G01N 21/47; G01N 21/9501; G01N 21/9503
USPC ............. 356/327.1–327.5, 394; 382/141, 107
See application file for complete search history.

(56) References Cited

U.S. PATENT DOCUMENTS 5,216,481 A  *  6/1993  Minato ....................... 356/239.1
5,416,594 A  *  5/1995  Gross et al. ................ 356/237.5
(Continued)

FOREIGN PATENT DOCUMENTS

EP          2088763        8/2009
KR       20040024795       3/2004

OTHER PUBLICATIONS

Anonymous: "Altasight, Double Side Inspection, Dark Field Inspection", [Online] Oct. 2008, URL: http://www.altatech-sc.com/pdf/specifications_altasight_200_300.pdf.
(Continued)

*Primary Examiner* — Sang Nguyen
(74) *Attorney, Agent, or Firm* — Meyertons, Hood, Kivlin, Kowert & Goetzel, P.C.; Eric B. Meyertons

(57) ABSTRACT

Device for inspecting defects in semiconductor wafers, comprising a member for detecting surface defects using variations in the slope of a surface of the wafer, a member for detecting surface defects using variations in the light intensity reflected by a surface of the wafer, at a plurality of points, a member for detecting light intensity scattered by the surface of the wafer, a light source, and a detecting and classifying mechanism connected upstream of said detecting members.

14 Claims, 12 Drawing Sheets

(56) References Cited

U.S. PATENT DOCUMENTS

| | | | |
|---|---|---|---|
| 5,734,742 A * | 3/1998 | Asaeda et al. | 382/141 |
| 7,105,848 B2 * | 9/2006 | Guha et al. | 250/559.45 |
| 7,259,869 B2 * | 8/2007 | Hwang et al. | 356/511 |
| 2003/0147128 A1 | 8/2003 | Shafer et al. | |
| 2004/0032581 A1 | 2/2004 | Nikoonahad et al. | |
| 2004/0169850 A1 | 9/2004 | Meeks | |
| 2005/0134842 A1 * | 6/2005 | Savareigo et al. | 356/237.5 |
| 2007/0229815 A1 | 10/2007 | Farrar et al. | |
| 2008/0007726 A1 | 1/2008 | Fairley et al. | |
| 2009/0051930 A1 | 2/2009 | Moulin | |
| 2009/0091768 A1 * | 4/2009 | Itoh | 356/611 |
| 2009/0195786 A1 | 8/2009 | Gastaldo | |
| 2011/0128371 A1 | 6/2011 | Gastaldo | |
| 2012/0013899 A1 * | 1/2012 | Amanullah | 356/237.5 |
| 2012/0057155 A1 | 3/2012 | Gastaldo | |

OTHER PUBLICATIONS

Anonymous: "Altatech Adds Double Side Option and Darkfield Inspection to Altasight, High Throughput Wafer Macro Inspection System", Oct. 6, 2008, URL:http://electronics.wesrch.com/paper-details/press-paper-EL1SE15D8YMFA-altatech-adds-double-side-option-and-darkfield-inspection-to-altasight-high-throughput-wafer-macro-inspection-system.

\* cited by examiner

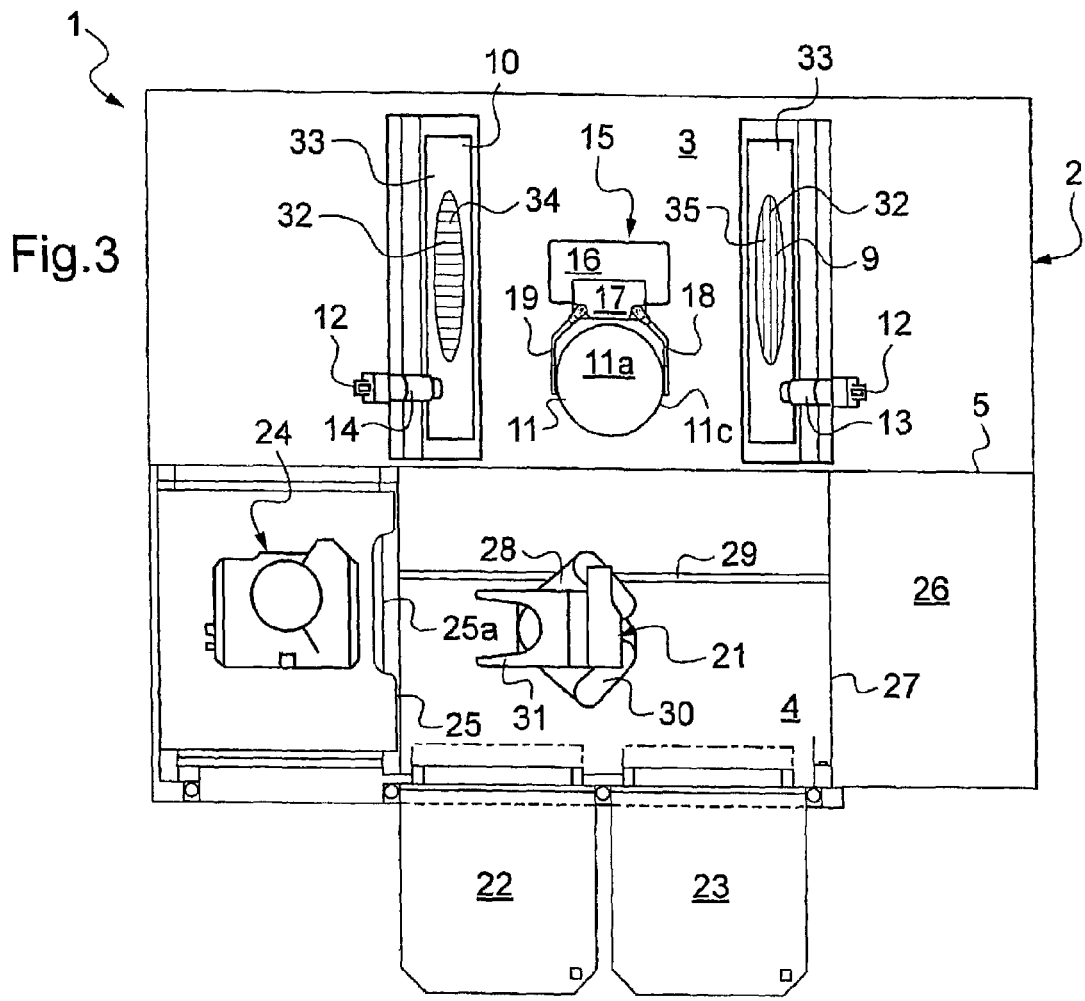
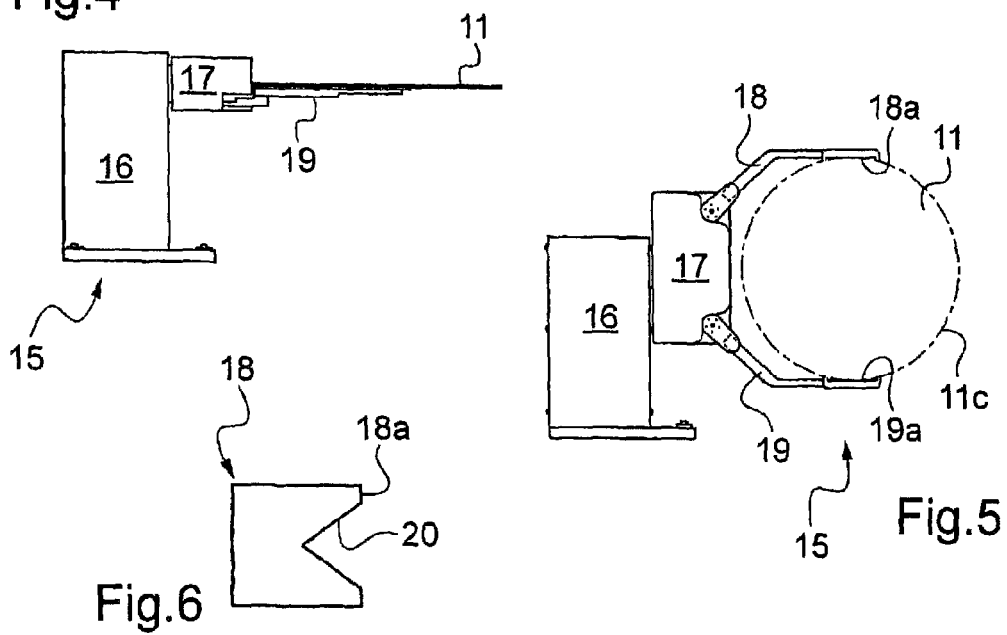

DEVICE AND METHOD FOR INSPECTING MOVING SEMICONDUCTOR WAFERS

PRIORITY CLAIM

This application is a 371 of PCT Application PCT/FR2011/000273, filed May 4, 2011, which claims priority to French Patent Application No. 1001958, filed May 6, 2010.

BACKGROUND OF THE INVENTION

1. Field of the Invention

The invention relates to the field of the inspection and checking of semiconductor wafers or substrates during or after manufacture, or when manufacturing integrated circuits.

2. Description of the Relevant Art

The tendency to increase the diameters of semiconductor wafers means that they have to be handled with extreme care and are increasingly fragile. In addition to this, the increasingly finer etching of patterns on semiconductor wafers makes each component of the wafer increasingly sensitive to manufacturing defects. Conventionally semiconductor wafers are inspected visually by an operator. The human eye is in fact capable of discerning relatively small defects on semiconductor wafers, which to an inexperienced observer have the appearance of a mirror. The higher the quality of manufacture, the more the human eye is capable of identifying small defects. The development of etching techniques towards ever-increasing fineness means that the human eye is reaching its limits, in particular for certain types of defects.

The task of visually inspecting semiconductor wafers is slow, tedious and onerous. In a clean room in which semiconductor wafers are manufactured it is desirable that human presence, a major source of contamination, should be reduced. Inspection machines are generally slow, have relatively poor performance and depend on an operator (and the results are therefore poorly reproducible). Finally, visual inspection does not give rise to sufficient statistical data on the positions, in particular in the plane of the wafer, sizes or types of defects, which is desirable for the statistical monitoring of processes and for searching for the causes of defects or problems.

SUMMARY OF THE INVENTION

The invention will improve this situation.

The device for inspecting defects in semiconductor wafers comprises a member for detecting surface defects based on variations in the slope of a surface of the wafer, a member for detecting surface defects from variations in the intensity of light reflected by a surface of the wafer, a member for detecting the intensity of light diffused by the surface of the wafer at a plurality of points, several light sources and a detection and classification mechanism mounted downstream of these detection members.

The first common light source may comprise a member projecting onto the surface of the wafer, and a pattern comprising an alternation of continuous light fringes and dark bands. The projection member may comprise a screen having a luminosity of at least 300 cd/cm$^2$. The device may comprise an image capture detector which is common to the said detection members. The said image capture member may be capable of detecting the displacement of fringes reflected by the substrate. The member for detecting surface defects based on variations in reflected light intensity may comprise a member calculating the intensity at a plurality of points in the image to generate an image of the reflected intensities. The detection and classification mechanism may comprise a classification grid on the basis of which a defect is either visible or not in the image of the reflected intensities, and is visible or not in an image of the variations in the slope of the wafer surface. The inspection device may form part of a machine comprising a wafer transport arm fitted with at least one wafer supporting member, a clamp for seizing wafers having two arms at a distance configured to hold opposite edges of the wafer, the clamp being rotatably mounted on a shaft so that it can turn the wafer between a substantially horizontal position and a substantially vertical position, and at least two inspection systems located on either side of the wafer in a substantially vertical position, symmetrically with respect to the plane passing through the wafer. The detection and classification mechanism may be connected to an output from the said inspection system, the classification grid taking into account whether a defect is or is not visible on the two surfaces of the wafer at locations close to each other. The machine may be independent of the inspection device. In fact the inspection system offers output images from which the detection and classification system performs an analysis to provide a resultant file comprising the nature, position and characteristics of the defects (such as their size, amplitude, etc.) as an output, together with an image of the zone comprising the defect. This analysis may be performed directly after production of the image or subsequently in a remote station to which the image files obtained are delivered. This process is described in document FR2931295.

The semiconductor wafer inspection device may comprise at least one wafer transport arm provided with at least one wafer supporting member. The said arm is configured to move at least one wafer along a trajectory comprising at least one substantially straight part. The at least one supporting member may define a supporting surface to hold the wafer substantially horizontal. The device may comprise at least one linear time delay integration camera located above the transport arm. The camera may have a field intersecting the straight part of the said trajectory so that the top surface of a semiconductor wafer is observed by the said camera as it moves along a straight part of the trajectory. The device may comprise at least one linear camera located above the trajectory. The device may comprise one or more linear cameras located beneath the trajectory to observe an underside of the wafer, the supporting members having a first spacing on an outgoing path and a second spacing different from the first spacing or a different shape from the first shape on a return path, allowing almost all of the undersurface of the wafer to be inspected, part along the outgoing path and a complementary part during the return path of the wafer along the straight part of the trajectory. The device may comprise two wafer transport arms fitted with supporting members, the supporting members of a first arm having a different spacing or a different shape from the supporting members of the second arm, the first arm being configured to perform an outward movement of a wafer, the return movement being carried out by the second arm thus allowing inspection of all the undersurface of the wafer, part during the outward path and part during the return path. The camera may comprise a rectangular matrix of pixels, for example comprising more than 2000 pixels in length and more than 48 pixels in width, and a summing member to sum the pixels in one width when inspecting a surface of a semiconductor wafer. The camera or cameras may be sensitive to ultraviolet radiation. The device may comprise a light source comprising a bar of electroluminescent diodes.

The device may comprise an on-board semiconductor wafer inspection system comprising a chromatic confocal microscope provided with lighting means and analysis means. The lighting means may comprise a polychromatic light source, a slit and an axial chromatic dispersion objective comprising a lens made of at least of a material whose Abbe number is less than 50. The analysis means may comprise the said objective, a chromatic filtering slit and a light intensity sensor in that order. The slit of the lighting means and the slit of the analysis means may be located substantially at the same optical distance from the edge of the wafer being inspected. The detection and classification mechanism may be connected to an output of the on-board inspection system. The classification grid may take into account whether a defect is or is not visible on an image provided by the on-board inspection system. The slit of the lighting means may form a linearising member. The light source may comprise a set of electroluminescent diodes and means for rendering the light intensity along the line uniform.

The process of inspecting semiconductor wafer defects comprises the following stages: variations in the slope of a surface of the wafer are measured by a first surface defect detection member, variations in the intensity of the light reflected by a surface of the wafer are measured by the same member in the course of the same acquisition, the said surface of the wafer being illuminated by a common light source, and surface defects are classified by a detection classification mechanism mounted downstream of the said detection members.

A process for inspecting defects and semiconductor wafers may comprise the stages of measuring variations in the slope of a surface of the wafer by means of a first surface defect detection member, measuring variations in the intensity of the light reflected by a surface of the wafer in a second surface defect detection member, the said surface of the wafer being illuminated by a light source, and classification of the surface defects by a detection and classification mechanism mounted downstream of the said detection members.

The first surface defect detection member and the second surface defect detection member may be active concurrently during the course of inspecting another property of the said wafer.

A wafer resting on at least one supporting arm attached to a transport arm may be moved in a trajectory comprising at least one straight part. During a straight part of the trajectory at least one linear time delay integration camera can perform an observation of the top surface of the wafer. The inspection may be performed before and/or after a static inspection.

The following stages may be provided: a semiconductor wafer resting on at least one supporting member attached to a transport arm is moved along a trajectory comprising at least one straight part, and in the course of the straight part of the trajectory at least one linear time delay integration camera performs an observation on the top surface of the wafer.

The invention will be better understood from a reading of the detailed description of a number of embodiments described by way of examples which are in no way restrictive and are illustrated by the appended drawings in which:

BRIEF DESCRIPTION OF THE DRAWINGS

FIG. 3 is a view from above of the machine in FIG. 1;

FIG. 4 is a diagrammatical view from the side of the clamp in a first position;

FIG. 5 is a diagrammatical view from the side of the clamp in a second position;

FIG. 6 is a view in transverse cross-section of one arm of the clamp;

DETAILED DESCRIPTION OF THE PREFERRED EMBODIMENTS

Figure 1:
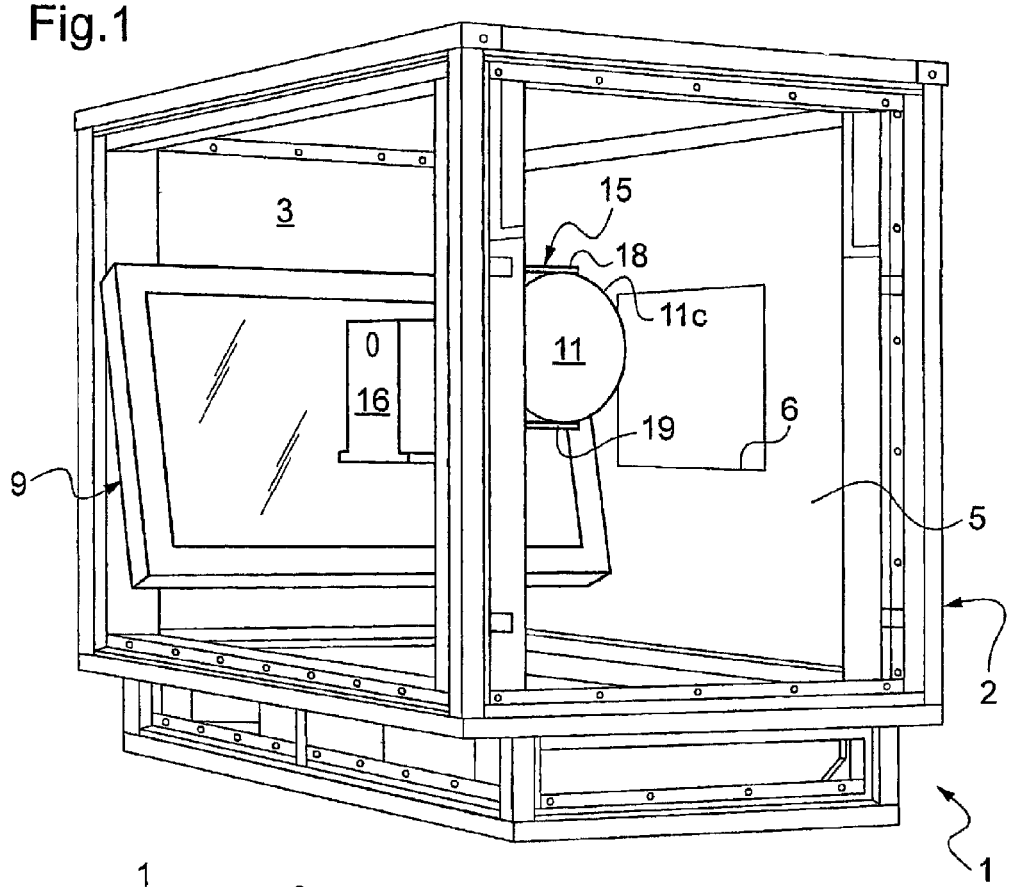
FIG. 1 is a diagrammatical perspective view of an inspection machine for flat discs, such as semiconductor wafers.

In general present-day inspection machines are designed for semiconductor wafers in a horizontal position resting on a plate, see US 2008/7726, JP 100 56 046 and KR 2004 0024795. The same applies to document EP 1 194 803 which also describes a complex catadioptric structure. The solution generally adopted comprises using a reference surface of better flatness than the measurable surface on which the wafer is placed or held while the measurement is made. This reference surface is in general that of a solid support. The contact between that surface and the wafer is a source of contamination of the back surface. In addition to this, this method masks the back surface while the front surface is being measured.

The applicant has developed a machine for inspecting wafers in a static vertical position, see FR 293 1295. Excellent sensitivity in defect detection perpendicularly to the plane of the wafer is achieved.

Wishing to achieve excellent sensitivity in defect detection parallel to the plane of the wafer at high rates, the Applicant has designed a machine for inspecting wafers on the fly. Inspection on the fly makes it possible to maintain the speed of adjacent processes, in particular upstream and downstream. Inspection takes place concurrently. In addition to this, the search for high sensitivity parallel to the plane of the wafer has made it possible to hold the wafer in a horizontal position. The Applicant became aware that concurrent inspection in a horizontal position could make use of movements of the wafer between existing machines, particularly in the machine according to FR 2931295, to which the reader is invited to refer. The wafer is moved in a substantially horizontal position during inspection. Here, substantially vertical means to within +/−1°. The opposing surfaces of the wafer are referred to as the top and bottom by convention, even when the wafer is in the vertical position, with reference to the horizontal position of the wafer supported by the fork during movement.

The supporting members provided to support a wafer may form a fork. The supporting members may thus move the wafer in a horizontal position while hiding part of the bottom surface of the wafer and leaving another part free. The fork provides good mechanical stability for the semiconductor wafer and deformation under its own weight which is within acceptable limits in the course of examination during movement. The transport arm may comprise at least two articulation axes. The transport arm may be supported by a turret. The turret may support two wafer transport arms. The turret may be mounted to move laterally on a slider. A turret having two transport arms can optimise movement of wafers between a wafer store and the seizing clamp.

The device may comprise a control unit configured to control the taking of images by the camera or cameras, and if necessary illumination through at least one light source. The control unit may comprise at least one output connected to a camera and at least one output connected to the corresponding light source to synchronise the camera and the light source. The light source may comprise a bar of electroluminescent diodes.

Each image may be taken during an exposure time of the order of between 100 milliseconds and 3 seconds. The transfer time from the cameras may be of the order of between 50 milliseconds and 1 second. The device may comprise at least one linear camera located above the trajectory. In the case where several cameras are used, each will be used for inspection of part of the surface in order to improve the resolution of the system and the sensitivity of defect detection.

Inspection may be carried out on the basis of a device according to patent application FR2914422, to which the reader is invited to refer, modified by the addition of a surface defect detection member based on variations in the intensity of the light reflected by a surface of the wafer. The said member may comprise a calculation module receiving data from a common sensor with the surface defects detection member based on variations in the slope of a surface of the wafer. The common sensor may comprise a camera, in particular of the CCD type. The light source common to two detection members may comprise a video screen receiving a pattern emission signal.

In one embodiment one or more time delay integration cameras, also known by the acronym "TDI" for "time delay integration", may also be used. This type of camera is described in document EP288763. A TDI camera comprises a matrix of sensor elements and a compensation block configured to compensate for the movement due to movement of the wafer during the exposure time. The charges generated by the sensor elements are moved virtually at the same speed. Movement may be performed on reading the matrix of sensor elements through an offset reading register. The offset may be calculated on the basis of the speed of movement of the wafer.

In this embodiment the surface of the wafer is illuminated with an intense lighting system which may be based on LEDs. The lighting system is focused on the area opposite the TDI camera. The beam is orientated in such a way that light directly reflected from the surface lies outside the camera aperture. In this case, the camera will only detect light diffused by the surface or by elements present on it, whether they belong to the substrate or whether they are attached to the surface.

The device may comprise a linear camera located beneath the trajectory to observe an undersurface of the wafer. Supporting members may have a first gap or a first shape along one outward path and a second different spacing or different shape from the first spacing or first shape along a return path. All the undersurface of the wafer may be inspected, part during the outward movement and an at least complementary part during the return movement of the wafer along the straight part of the trajectory.

The device may comprise two wafer transport arms fitted with supporting members, the supporting members of a first arm having a spacing which is different from the supporting members of the second arm, the first arm being configured to make an outward movement of a wafer, the return movement being performed by the second arm, thus making it possible for all the undersurface of the wafer to be inspected, part during the outward movement and part during the return movement.

The camera or cameras may be sensitive to ultraviolet radiation. The camera may comprise a rectangular matrix of pixels comprising more than 2000 pixels in length and 100 pixels in width, and a summing member to sum the pixels in one width when inspecting a surface of a semiconductor wafer.

Inspection is performed before and/or after static inspection, particularly as the wafer moves towards or from static inspection. When moving from static inspection, the part of the undersurface of the wafer hidden by the transport members may be different from the part hidden by the transport members when moving towards static inspection. The spacing or shape of the transport members may differ in the outward and return journeys. The relative position of the transport members in relation to the undersurface of the wafer may be different when moving outwards and moving back.

The inspection device may form part of a machine comprising a wafer transport arm fitted with at least one wafer support member, a clamp for seizing wafers having two arms at a distance configured to hold opposite edges of the wafer, the clamp being rotatably mounted on a shaft so that it can turn the wafer between a substantially horizontal position and a substantially vertical position, and at least one inspection system located on either side, a system located symmetrically in relation to the plane passing through the wafer opposite it. Each inspection system may comprise at least one light source and at least one camera located on one side and at least one light source, each camera being positioned to capture the light reflected by the surface of the wafer opposite to it and each light source being positioned to emit an incident beam towards the said surface. The transport arm may comprise at least two articulation axes and be supported by a turret supporting at least one wafer transport arm, the turret being mounted so as to move laterally on a slider. Each arm of the clamp may have a groove, in particular of a general V shape, provided in a surface opposite the other arm. At least one of the arms may be pivotally mounted along an axis which is substantially perpendicular to the plane of the wafer held between the said arms. The transport members may have lateral dimensions which are smaller than the opening between the arms of the clamp. Each light source may comprise a monitor, in particular an LCD screen. The camera may be located above the light source. A control unit may be configured to control the display of parallel rays by light sources. The control unit may comprise at least one output connected to a camera and at least one output connected to the corresponding light source to synchronise the camera and the light source. The control unit may be configured to control an oval area lit by the light source and a dark external edge. The control unit may be configured to control the display of different colours simultaneously by the light sources. The control unit may be configured to control alternating lighting by the said light sources.

When inspecting semiconductor wafers, a semiconductor wafer under inspection is delivered by at least one supporting member attached to a transport arm, the distant arms forming part of a clamp seizing opposite edges of the wafer, the clamp turning about a shaft causing the wafer to move from a substantially horizontal position to a substantially vertical position, a light source located at the side of the wafer and a light source located on the other side of the wafer symmetrically in relation to a plane passing through the said wafer emitting an incident beam towards the surface of the wafer opposite each light source respectively, and a camera located on one side of the wafer and a camera located on the other side capturing the light reflected by the surface of the wafer opposite. The time delay integration linear camera takes images during the outward and return transport stages of the supporting member.

Figure 2:
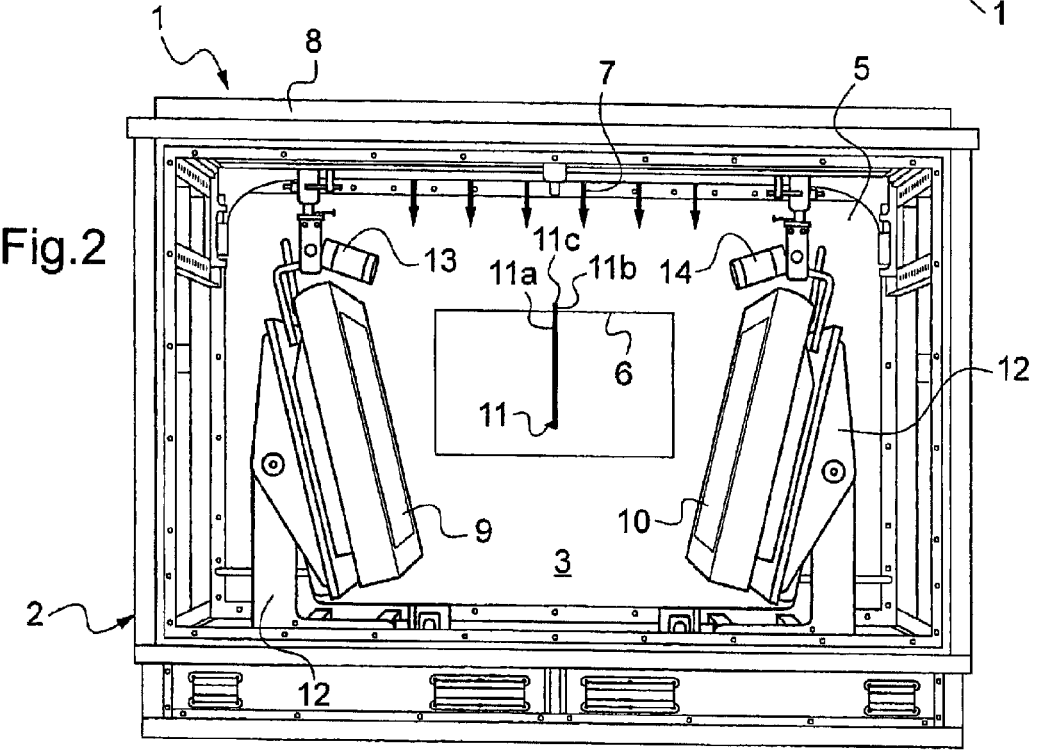
FIG. 2 is a front view in elevation of the machine in FIG. 1, framework and cover members having been removed.

In FIGS. 1 to 3 inspection machine 1 has been illustrated with the cover open. More specifically, in FIG. 1 the front cover and two of the side covers are open. In FIG. 2 the front cover is open. In FIG. 3 the top cover is open. Of course inspection machine 1 has its covers closed in the operating condition. The covers are opaque to prevent parasitic light which might disturb the cameras from entering. In addition to this, in FIG. 1 one of the two screens, the corresponding camera and the clamp support have been omitted so that the other parts may better be seen. Likewise in FIG. 2 the clamp and the clamp support have been omitted, the substrate being shown in the substantially vertical inspection position.

As may be seen in FIGS. 1 to 5, inspection machine 1 comprises a frame 2, for example of the mechanically welded type forming an inspection chamber 3 and a feed chamber 4 separated by a partition wall 5 pierced by a window 6. Frame 2 is covered by the covers. Inspection chamber 3 has a symmetrical structure in relation to the vertical plane passing through the middle of FIGS. 2 and 3. Inspection machine 1 comprises a filtered air feed 8 of the laminar type which makes it possible to generate a downward movement of air in chamber 3, as shown by arrows 7. Air feed 8 also forms the top wall of chamber 3. The floor of the measuring chamber comprises a stack of 2 grids, one of which may be offset from the other, this being used to control the flow of air leaving by that opening, and thus controlling the excess pressure in the measurement chamber.

Inspection machine 1 comprises two video screens 9 and 10 symmetrically mounted in relation to a vertical plane passing through the centre of inspection machine 1 or again passing through substrate 11 under inspection which is held in the vertical position, see FIGS. 1 and 2. Each screen 9, 10 rests on a support 12, for example of the articulated type enabling screen 9 and 10 to be orientated about an axis substantially parallel to the plane of substrate 11, for example a substantially horizontal axis, and for the position of screen 9, 10 to be adjusted in lateral movement in relation to the surface being measured. Screens 9 and 10 are mounted opposite each other at a distance and are slightly orientated upwards, for example through an angle of between 10 and 30°. Screens 9 and 10 may be of the LCD type. Screens 9, 10 have a height of more than 1.6 times the diameter of the substrate being inspected, for example a height of 54 cm for a substrate of 300 mm diameter and a height of 72 cm for a substrate of 450 mm diameter.

The sides of the illumination screen are conventionally referred to as height and width. By height is meant the smaller dimension of the screen's display area, with reference to the orientation of the screen when using a conventional video display unit.

The inspection machine also comprises two cameras 13, 14 located in inspection chamber 3. Cameras 13, 14 may be supported by supports 12. One support 12 is common to a screen, 9 or 10, and a camera 13 or 14. Camera 13 is hidden in FIG. 1 by an upright of frame 2. Cameras 13, 14 may also be adjusted in position, in particular in height, width and length, length corresponding to the horizontal distance in relation to substrate 11. Cameras 13 and 14 may also be adjusted in angular orientation. The cameras may be of the CCD (Charge Coupled Device) type or CMOS (Complementary Metal Oxide Semiconductor) type. Screen 9 and camera 13 form a first inspection system. Screen 10 and camera 14 form a second inspection system. The first and second inspection systems are symmetrical.

The respective positions of screen 9, substrate 11 and camera 13 on one side, and screen 10, substrate 11 and camera 14 on the other side of inspection chamber 3 are selected so that each screen 9, 10 emits an incident beam reaching substrate 11 on its corresponding surface 11a, 11b respectively and camera 13, 14 captures the beam reflected by surface 11a, 11b. Surfaces 11a and 11b are parallel. The incident beam does not reach all of substrate 11. The relative positions are selected in such a way that surface 11a, 11b is sufficiently lit to allow camera 13, 14 to detect a light signal that is representative of defects in surface 11a, 11b. The luminosity and contrast of screen 9, 10 are adjusted to high levels to encourage the detection of defects by cameras 13, 14. Furthermore, the inactive surfaces of chamber 3 have maximum absorption at the wavelengths used. In other words, the inactive surfaces of inspection chamber 3 are black in colour. Disturbance of cameras 13, 14 is restricted in this way.

As cameras 13, 14 are inclined in relation to the normal to surfaces 11a, 11b, with slight distortion as the distance between the top extremity of surface 11a and the objective of the camera is less than the distance between the bottom extremity of surface 11a and the objective of camera 13. The same applies to camera 14 in relation to surface 11b opposite to it. For this purpose cameras 13, 14 may comprise a tilting objective which makes it possible to obtain a clear image of all the surface area inspected by tilting the focal plane.

Inspection machine 1 comprises a clamp 15 holding substrate 11. Clamp 15, which may be seen in FIGS. 1 and 3, is shown in greater detail on FIGS. 4 and 5 providing substrate 11 with a horizontal receiving position and a vertical inspection position respectively. Clamp 15 comprises a base 16 resting on frame 2, a turret 17 and two arms 18 and 19. Base 16 may have the general shape of a rectangular body. Turret 17 is articulated on base 16 on an axis which is substantially horizontal and passes through window 6. The turret is designed to rotate through at least 90°. Rotation of 180° may allow substrate 11 to be turned over, and this may be useful in some applications. Turret 17 may be rotated by an electromechanical drive system located in base 16, for example a stepping motor.

Arms 18 and 19 are symmetrical in relation to a plane normal to substrate 11 when substrate 11 is carried by arms 18 and 19. Each arm 18, 19 is articulated on turret 17 about its own axis, which is offset from the pivot axis of turret 17 and normal to substrate 11. In a variant, arms 18 and 19 may be coaxial. In another variant, one of the arms is stationary in relation to turret 17 and the other arm is articulated. Turret 17 comprises a member driving arms 18, 19, for example in the form of two stepping motors or again one stepping motor and a gear enabling arms 18 and 19 to remain symmetrical whatever their angular position. Arms 18 and 19 can pivot between two working positions, an open position used to approach or move away from substrate 11, and a position gripping the outer edge 11c of substrate 11. FIGS. 4 and 5 show the gripping position.

More particularly, each arm 18, 19 is of elbowed shape in such a way that the dimensions of turret 17 are less than the diameter of substrate 11. In other words, arms 18, 19 have the shape of a circumflex accent. Arms 18, 19 each have an inner face 18a, 19a opposite the inner face of the other arm 19, 18 and designed to come into contact with the outer edge 11c of substrate 11. Inner surface 18a, 19a has a groove 20 running parallel to the pivot axis of turret 17. Groove 20, which can be seen in FIG. 6, may have a V-shaped transverse cross-section or alternatively a semi-circular or ogival shape to act together conveniently with the outer edge 11c of substrate 11 and provide good holding in both the horizontal position of substrate 11 illustrated in FIG. 4 and the vertical position illustrated in FIG. 5 and in intermediate positions, with little force, reducing the deformation of substrate 11, in particular buckling in the inspection position, to negligible amounts.

Inspection machine 1 comprises a substrate handling member 21 designed to bring a substrate 11 to clamp 15 before inspection and to discharge the substrate from clamp 15 after inspection. Handling member 21 is located in feed chamber 4. Handling member 21 may take the form of a robot provided with a working member capable of passing through window 6 provided in partition wall 5.

Inspection machine 1 comprises two movable containers 22, 23 to store a plurality of substrates 11. Containers 22, 23 are supported by a wall of chamber 4 on the side opposite internal partition wall 5. Containers 22, 23 may be of the self-closing type so as to close when separated from inspection machine 1. Likewise the wall of handling chamber 4 is provided with a window opposite containers 22, 23, with an automatic cover closing off feed chamber 4 before containers 22, 23 are completely removed. Contamination of substrates 11 and the chambers of inspection machine 1 by dust is thus restricted.

Inspection machine 1 comprises a prealignment member 24 for substrates 11. Prealignment member 24 may be located along partition wall 5 at a longitudinal extremity of feed chamber 4. In addition to this, inspection machine 1 comprises a control and processing unit 26 which may take the form of an electronic drawer. Control unit 26 is located at the extremity of feed chamber 4 opposite prealignment member 24 with a separating partition wall 27. Processing unit 26 may also be in contact with partition wall 5. Control unit 26 is connected to screens 9 and 10, cameras 13 and 14, clamp 15 and handling member 21.

Handling member 21 comprises a turret 28 which is capable of moving laterally in relation to frame 2 along an axis parallel to partition wall 5. Thus, handling member 21 may approach opening 25a towards prealignment member 24 in one position and come alongside window 6, opposite clamp 15 in another position, or again alongside container 22, or opposite container 23. Turret 28 can move along a slider 29 which is of one piece with frame 2. Handling member 21 comprises an arm 30 having two articulation axes supported by turret 28 and a fork 31 supported by the extremity of arm 30 opposite turret 28. The articulation axes of arm 30 may be substantially vertical. In other words, arm 30 has two articulation axes which are parallel to each other and normal to the plane of a substrate 11 resting on fork 31.

Figure 7:
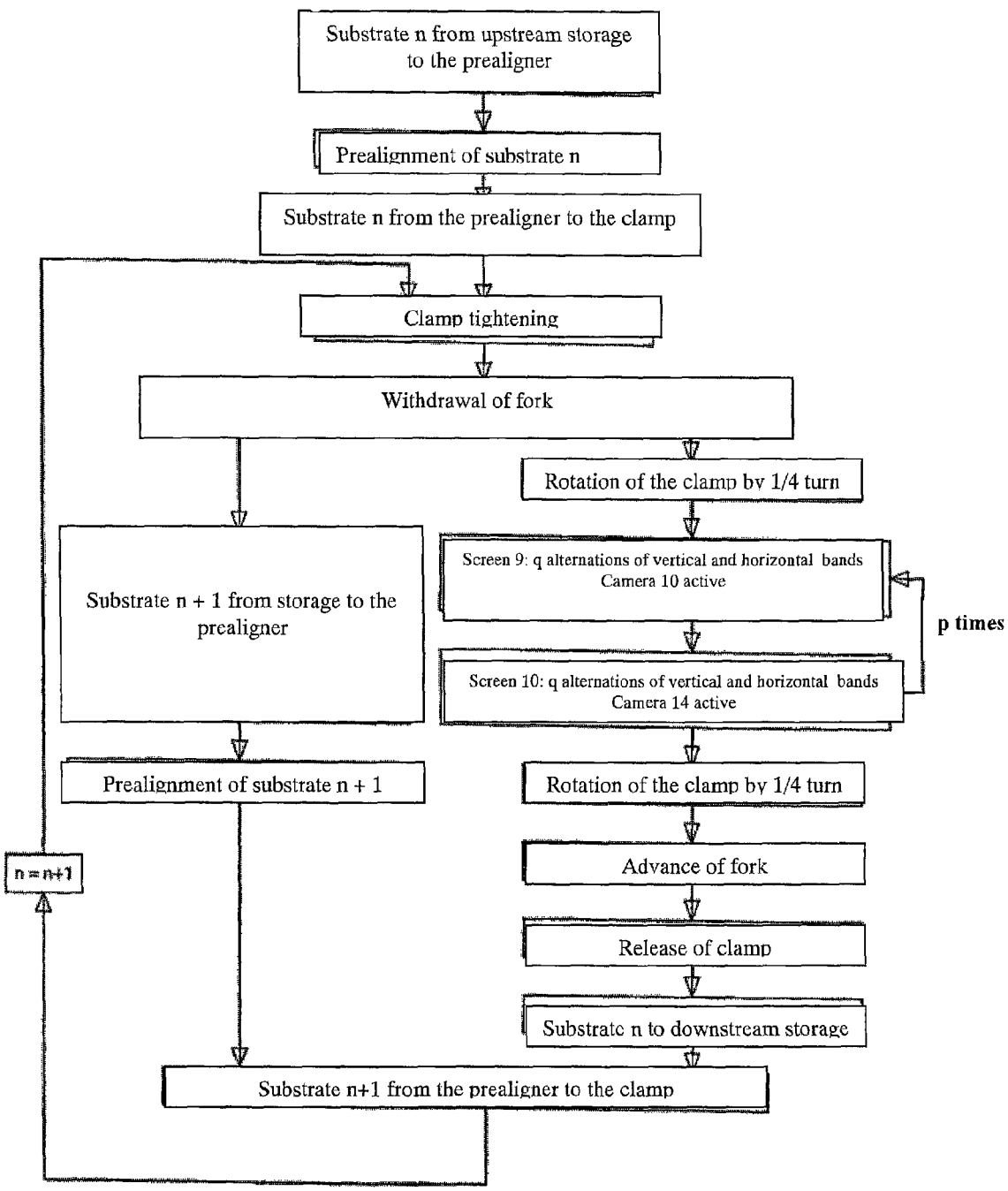
FIGS. 7 and 8 are flow charts of stages in the process.

When in operation, see FIG. 7, control unit 26 controls handling member 21, clamp 15, screens 9 and 10 and cameras 13 and 14. Handling member 21 moves opposite container 22 containing a plurality of substrates requiring inspection. Fork 31 passes beneath the substrate 11 then lifts substrate 11 through between a few hundred microns and a few millimeters and withdraws from container 22 supporting substrate 11. Handling member 21 then moves substrate 11 to prealignment member 24 which ensures that substrate 11 is suitably positioned, for example by means of three fingers driven in a radial movement and coming into contact with the outer edge 11c of substrate 11. Then fork 31 picks up substrate 11 and causes it to pass through window 6 to place it between the arms 18 and 19 of clamp 15. Fork 31 is very slightly below arms 18 and 19 so that substrate 11 is located at the level of arms 18 and 19. Arms 18 and 19 clamp the outer edge 11c of substrate 11. Fork 31 lowers to disengage from substrate 11, which is from then on held between arms 18 and 19, in particular in grooves 20. Handling member 21 then retracts fork 31, for example into handling chamber 4.

Substrate 11 held between clamps 18 and 19 in a position which is originally substantially horizontal is turned through a quarter turn to move it into the substantially vertical position illustrated in FIG. 1. Control unit 26 then proceeds with the inspection proper by causing surface 11a of substrate 11 immobilised by clamp 15 to be lit by screen 9. Screen 9 displays substantially vertical alternate light and black rays, then substantially horizontal alternate light (in white or colour) and black rays 35, doing so q times, where q is between 1 and 20. Simultaneously, camera 13 captures images, for example during a period of between 100 and 3000 milliseconds. Camera 13 may take a succession of images for each type of ray. Screen 9 is then switched off and screen 10 is lit to illuminate surface 11b of substrate 11. Screen 10 displays rays similar to those of screen 9, in particular vertical rays 34, see FIG. 2. Camera 14 takes one or more images simultaneously. The images taken by cameras 13 and 14 are transferred to control unit 26 which carries out processing with a view to establishing the presence of any defects, particularly defects in the flatness or appearance of surfaces 11a and 11b of the substrate. This sequential manner of operation may advantageously be replaced by a simultaneous mode in which the screen/camera system inspecting the top surface and that inspecting the undersurface work independently and simultaneously.

In one embodiment, illumination is provided by all the surface of screens 9 and 10. The Applicant has found that it is useful to restrict lighting to an oval area 32 in screens 9 and 10 corresponding to the geometrical projection of surfaces 11a and 11b of substrate 11 respectively on screens 9 and 10. In this case, vertical rays 34 then horizontal rays 35 are displayed within oval area 32, the outer edge 33 of the screen remaining black. The quantity of light diffusing within inspection chamber 3 is reduced and disturbance of cameras 13 and 14, which can then provide a signal of improved quality, is reduced.

Subsequently, once the stage in which substrate 11 is immobile in a substantially vertical position has come to an end, turret 17 of clamp 15, controlled by control unit 26, substantially turns through a quarter turn to return substrate 11 to a substantially horizontal position. Fork 31 of handling member 21 advances between substrate 11 at a safe distance, for example of the order of several millimeters, then moves vertically rising at slow speed until it is close to undersurface 11b of substrate 11. Arms 18 and 19 then move from the clamping position to the open position, substrate 11 resting on fork 31.

Fork 11 leaves inspection chamber 3 and in moving towards feed chamber 4 places substrate 11 in container 22 and 23. The cycle can then be repeated. Of course, in order to increase the productivity of the inspection machine handling member 21 may be controlled to pick up a substrate 11 and carry it to prealignment member 24 during the stages in the course of which substrate 11 previously carried to clamp 15 is in the course of being inspected by cameras 13 and 14. As may be seen in the flowchart in FIG. 7, the stages of lighting by screen 9/10 and observation by camera 13, 14 may be repeated until sufficiently accurate data are obtained. The number of sub-stages p may be between 1 and 10.

Figure 8:
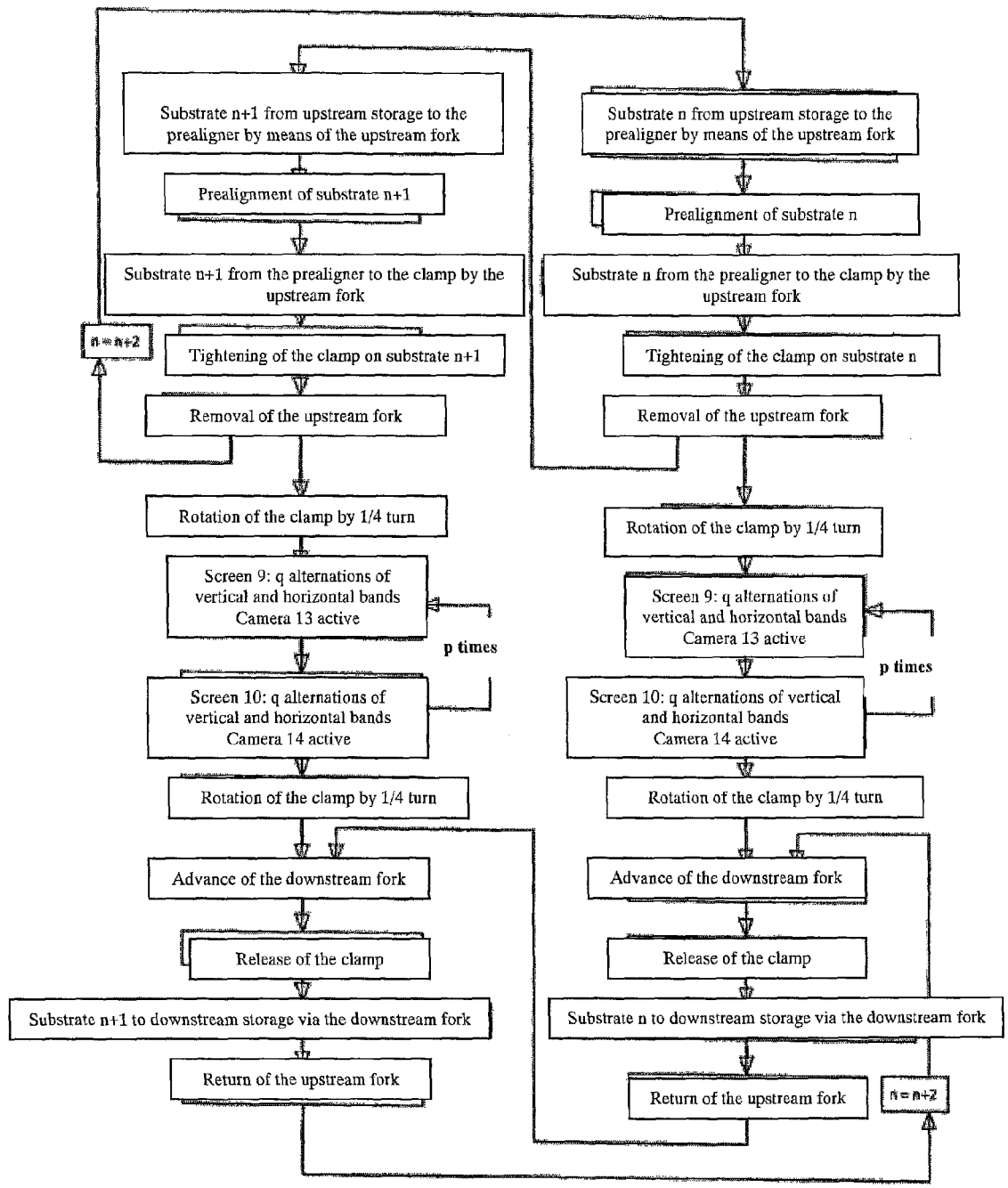
Figures 9, 10:
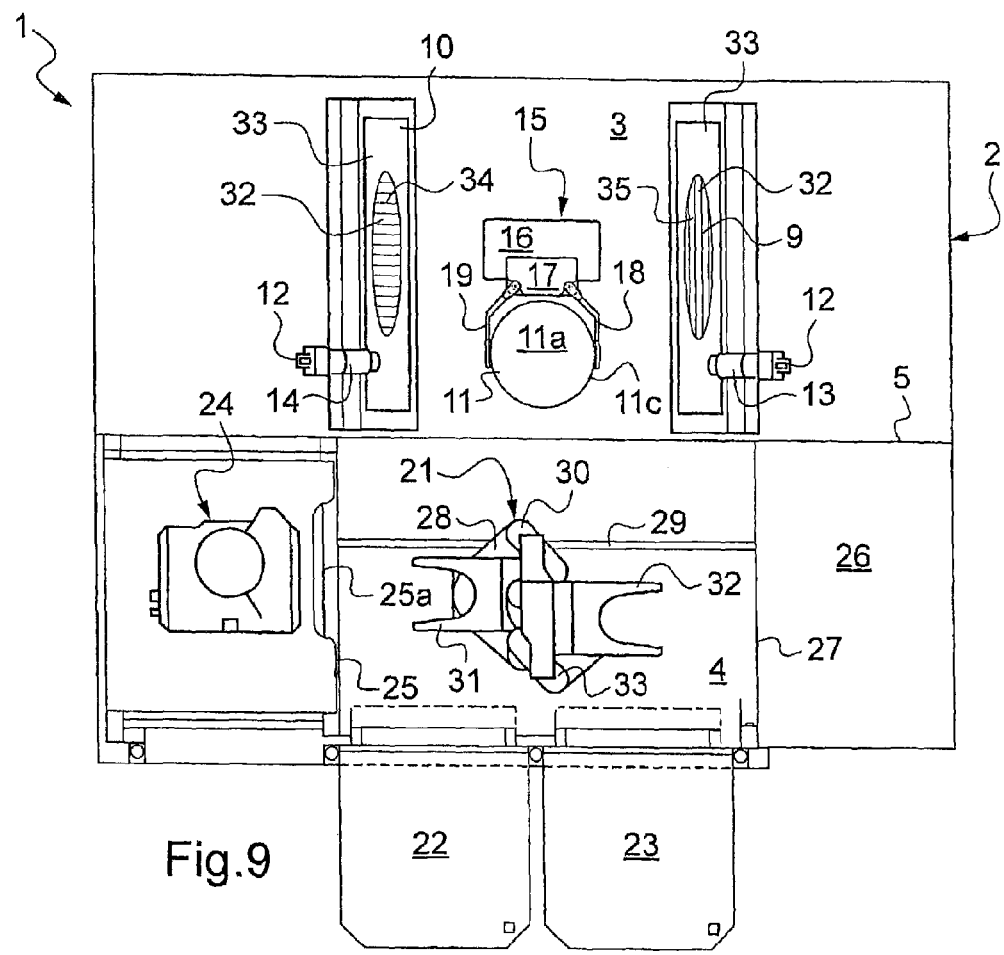
FIG. 9 is a view from above of an inspection machine for flat discs.
FIG. 10 is a diagrammatical view of a defect inspection assembly.

In the embodiment in FIG. 9, handling member 21 may be fitted with a turret 28 supporting two arms 30, 33 each provided with a fork 31, 32. The productivity of inspection machine 1 may then be improved by following the flowchart in FIG. 8, in that one of the forks, described as the upstream fork, can be dedicated to the stages of handling prior to inspection by cameras 13 and 14, while the additional fork described as the downstream fork can be dedicated to the stages of handling subsequent to inspection by cameras 13 and 14 to return inspected substrate 11 from clamp 15 into container 22 or 23.

Several stages may be performed simultaneously depending respectively on the time required for each stage and in particular the time for inspection by cameras 13 and 14. More particularly the upstream fork may remove a substrate from prealignment member 24 while the previous substrate is in the course of being inspected by cameras 13 and 14, the upstream fork then remaining awaiting removal of the preceding substrate by the downstream fork. As soon as the downstream fork has extracted previous substrate 11 from processing chamber 3 the upstream fork can insert the next substrate into treatment chamber 3. In other words the time between the two inspection stages by cameras 13 and 14 is reduced, and hence performance is increased.

Furthermore, the upstream fork has two handling operations to perform, delivery of substrate 11 to prealignment member 24 then delivery of substrate 11 to clamp 15, while the downstream fork has only one handling operation to perform, delivering inspected substrate 11 to downstream container 23. Control unit 26 may give priority to upstream fork 31, which will also help to slightly reduce the cycle time. Thus the downstream fork may remain with inspected substrate waiting to be put away, while the upstream fork performs another operation, for example taking a substrate from container 22 to deliver it to prealignment member 24, or again taking a substrate 11 from prealignment member 24.

Furthermore, control unit 26 may be configured to cause the light sources comprising screens 9 and 10 to operate simultaneously. Containers 22 and 23 may serve one as the upstream container and the other as the downstream container. Containers 22 and 23 may act one after the other, a substrate 11 taken from container 22 returning there after inspection, possibly in the same position.

Inspection member 40, see FIG. 10, comprises an inspection machine 1 equipped as above. Inspection member 40 additionally or alternatively comprises a member 45 for detecting surface defects from variations in the slope of a surface of a wafer, a member 41 for detecting surface defects from variations in the intensity of the light reflected by a surface of the wafer and a detection classification mechanism 42 mounted downstream of the said detection members. Detection member 45 comprises an image capture sensor 46 to detect fringes reflected by the substrate. Image capture sensor 46 may provide image data to detection member 41. Image capture sensor 46 may be a camera of the type [omission]. The image capture sensor may be a camera comprising a Kodak® detector. The image capture sensor may be capable of taking an image in an acquisition time of less than 250 ms, preferably less than 150 ms. Image capture detector 46 may take 10 to 14 images as a substrate moves within its field. It is thus possible to inspect at least 60 substrates per hour, preferably 70 or 80. Operations other than the acquisition of images, in particular transfer, are performed concurrently. In other words, an image is transferred during acquisition of the next image or an image of the opposite surface.

Detection member 41 comprises a light source. The light source is provided with a member for projecting light into the surface of wafer 11, for example a video screen, in particular of luminosity of at least 300 cd/cm², preferably in excess of 500 cd/cm², and a pattern displayed by the video screen. The pattern comprises an alternation of fringes of continuous light and dark bands. Detection and classification mechanism 42 is mounted downstream from detection member 41. Inspection member 40, see FIG. 10, may comprise a time delay integration camera 44. Inspection member 40 may comprise the system for inspecting the edges of semiconductor wafers 701.

Detection and classification mechanism 42 may comprise a defect criterion table indicating what types of defect will be found, may be found and will not be found using that type of inspection, see below. The Applicant has become aware that a given type of defect may be detected by one mode of inspection, may not be detected or again may be detected under certain conditions. This is mainly due to the morphology of the defects and their signature in relation to the technology used. Defects having relief have for example a signature which is visible with one technology, whereas defects having only surface absorption will not be visible through that technology. It may also happen that some defects of different types have comparable signatures if they are observed with one technology, whereas another technology can obtain different results. Combination of technologies therefore makes it possible to distinguish these defects through comparing the results obtained from each of the technologies. Table 1 below provides an example of one embodiment in which a zone which is not transferred during one stage of manufacture is detected by the inspection of reflectivity and possibly by single side topographic inspection, a non-traversing slip line is detected by single side topographic inspection, a traversing slip line is detected by two-sided surface topographic inspection, a hotspot appearing during the deposition of thin layers is detected by reflectivity inspection and by dark field time delay integration inspection, a tear is detected by reflectivity inspection and two-sided topographic inspection, a spot or local lack of uniformity in refractive index or thickness is detected by reflectivity inspection, marbling associated with a slow variation in thickness is detected by reflectivity inspection, a nick is detected by edge inspection, a fracture is detected by edge inspection and possibly by dark field time integration inspection, a small particle of a few microns is detected by dark field time integration inspection, a cleavage line is detected by dark field time integration inspection and by reflectivity inspection and by single-sided topographical inspection and by two-sided topographical inspection, a large particle of several tens of microns is detected by dark field time integration inspection and by reflectivity inspection and possibly by single-sided topographical inspection, a contact mark with a lifting device is detected by dark field time integration inspection and by single-sided topographical inspection, a narrow scratch is detected by dark field time integration inspection, a wide scratch is detected by dark field time integration inspection and reflectivity inspection and by single-sided topographical inspection, and a mark by the feed treatment chamber holding finger is detected by single-sided topographic inspection.

Edge Inspection

Figure 12:
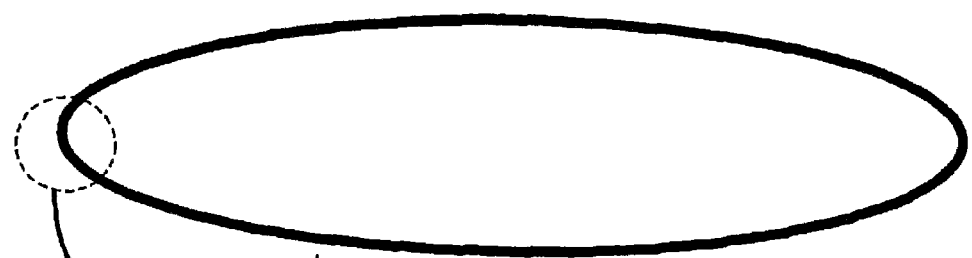
FIG. 12 is a diagrammatical view of a semiconductor wafer.
Figure 13:
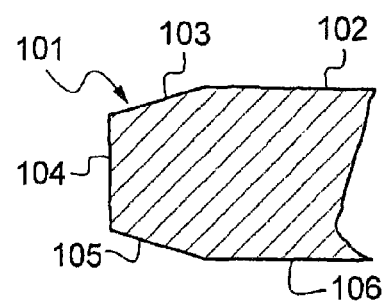
FIG. 13 is a detailed view of FIG. 12.

A slice of semiconductor substrate 101 is inspected by turning the substrate in front of a viewing system of the matrix or linear camera type. By slice of substrate is meant the edge 104 substantially perpendicular to the top and bottom surfaces of the substrate, the upper bevel or chamfer 103, the lower bevel or chamfer 105, the area close to upper edge 102 and the area close to lower edge 106, see FIGS. 12 and 13.

For sampling checks or for the analysis of areas limited to a small part of the edge surface, slow very high performance inspection systems with a small observation field and large magnification may be used. Among the slow systems confocal microscopy may be selected. However the acquisition rate of confocal microscopy equipment does not make it possible to use it in the systematic inspection of mass production as is practised in the semiconductor industry.

Now the applicant has found that the increase in the diameter of the substrates and the complexity of the manufacturing processes, through the succession of a large number of stages and heat treatments, increases the internal mechanical stresses to which they are subjected and consequently increases the risk of propagation of defects, for example microcracks located at the edge of the substrate. Furthermore, the increase in yield, in the meaning of the number of chips per substrate for the same diameter, results in chips being located close to the edges. Edge inspection is therefore of increasing interest. Chromatic coding is used in the context of measuring distance to control the focus on equipment for photolithography in the semiconductor field. Measurement of thickness or distance requires a chromatic analysis of the reflected light in order to convert this information into a geometric parameter for the object measured. This conversion is slow.

Edge inspection makes use of chromatic confocal microscopy based on confocal microscopy and on the use of the chromatic dispersion of the optical system used. In general, a confocal microscope mechanically readjusts the point of focus of the optics and from this deduces the morphology of the surface. This mechanical readjustment is slow and likely to give rise to breakdowns. Furthermore, as movements are generally associated with friction, they often prove to be the source of particles, which are undesirable in an environment in which microelectronic components are being produced.

As a result of the invention a narrow range of well-focused wavelengths are used, and this yields a clear image. Analysis of wavelengths makes it possible to determine, if desired, the distance between the confocal chromatic sensor and the object analysed. With an optical system having strong chromatic dispersion comprising at least one lens made of material having an Abbe number of less than 50, or even 35, different focuses are produced for different wavelengths. The focal point is therefore spatially spread and there is a great depth of field. The depth of field may attain several millimeters.

By retaining a wavelength or narrow range of wavelengths corresponding to well-focused wavelengths an optical autofocus system is obtained. This autofocus system may dispense with mechanical movement. This is achieved through slits located at the same optical distance from the surface being inspected or again the objective, given that the objective belongs to the lighting means and the analysis means at the same time. In this way it is possible to have multipoint acquisition each with the advantageous properties above. The lighting and analysis paths may be separated by a semi-reflecting sheet between the slit and the objective for the lighting path and between the objective and the chromatic filtering slit for the analysis path. The slit forms a linearising member.

A device 701 for inspecting the edges of semiconductor wafers comprises a chromatic confocal microscope provided with a lighting path and an analysis path. The lighting path comprises a polychromatic light source, a slit and an axial chromatic dispersion objective selected to have chromatic dispersion, comprising at least one lens made of a material having an Abbe number of less than 50. The analysis path comprises the same objective, a chromatic filtering slit and a light intensity sensor in that order. The slit of the lighting path and the slit of the analysis path are located at substantially the same optical distance from the edge of the wafer under inspection. In other words, these slits can be located at the same optical distance from the edge of the objective. In this way wavelengths which are not focused on the edge of the semiconductor wafer during inspection can be spatially filtered out.

A process for inspecting the edges of semiconductor wafers may comprise stages during which the edge is illuminated a polychromatic light source, the incident beam passing through a slot and through an objective providing dispersion comprising at least one lens made of a material having an Abbe number of less than 50, and collecting the reflected beam after it has passed through that objective and then through a chromatic filtering slit configured to spatially filter out wavelengths which are not focused on the edge of the semiconductor wafer. Gathering is performed by a light intensity sensor.

The light source may comprise a set of electroluminescent diodes, for example in the form of a bar, and a member for homogenising light intensity along the line. The device may comprise a processing unit connected to an output of the sensor to receive and analyse the light intensity signal. A plurality of light intensity sensors may be provided to inspect a plurality of facets of the said edge, the processing unit may comprise an assembler for the output data from the light intensity sensors giving rise to a file of inspection results for that plurality of sensors. The processing unit may comprise an edge defect discriminator generating a classification by type of defect, position, reflectivity, shape or dimensions. The device may comprise a chromatic analyser for the light back-diffused or reflected by an edge of the semiconductor wafer with an output connected to the processing unit. The processing unit then comprises an extractor generating distance data between the objective and the edge of the semiconductor wafer. The objective may have an optical diameter of less than 100 mm, which because of its smaller size may make it possible to incorporate the system in a restricted environment.

The surface which is to be inspected is located at a distance within the area of axial chromatic dispersion, in other words at a distance between the wavelength of the incident light having the shortest focal length and the wavelength of the incident light having the longest focal length. The device can be used to inspect a portion of the edge of the substrate independently of a focusing adjustment mechanism. Through continuous measurement of a portion as the substrate rotates an image of the complete periphery of the substrate can be obtained.

The inspection device uses the light intensity information provided by the sensor to provide a grey scale image with economical equipment and very quick acquisition, thus making it possible to have a system which is compatible with mass production. The device has an automatic autofocus function which makes it particularly simple, reliable and fast, in particular in comparison with conventional imaging systems. The device makes it possible to observe a large field comprising points whose distance in relation to the optical objective can vary more than in a conventional imaging system having the same magnification.

Optionally, the measurement of topography by the chromatic analysis of reflected light can be performed for more accurate applications at a lower rate, such as the subsequent analysis of detected defects. Measurements of topography may also be used to quantify edge loss, information which is particularly useful for substrates which are being reconditioned and therefore repolished.

The position of the objective with respect to the surface being inspected may be at a distance of between a few millimeters and a few centimeters. This makes the space close to the substrate less obstructed, a space which is generally used for handling the substrate by one or more robots. So that the maximum light can be collected for a given digital aperture, it is nevertheless desirable to maintain a small distance between the surface being inspected and the objective.

The rotation speed of the substrate may be between 0.1 and 10 revolutions per minute for a substrate 300 mm in diameter, for example between 1 and 10 revolutions per minute for the analysis of light intensity. This rotation speed would have to be adjusted for a substrate of different diameter in order to maintain a similar linear speed, for example in a range between 0.1 and 10 meters per second, more particularly between 1 and 10 meters per second for the analysis of light intensity.

The resolution of the sensor may be between 128 and 10,000 pixels. Resolution may be adjusted to the size of the defects sought and the desired rate. The light source may comprise an arc lamp of the xenon type, an incandescent lamp, a halogen lamp or an electroluminescent diode source. Electroluminescent diodes are advantageous in terms of lifetime, low consumption and low heating.

The incident light generated by the source then passes through a slit in the lighting system to linearise the beam. The assembly comprising the light source and the slit on the incident path comprises a linear light source. The incident beam then passes through a semi-reflecting plate and then through the objective in order to reach the surface being inspected. The beam reflected by the surface being inspected passes through the objective and the through the semi-reflecting sheet and leaves along an axis which is different from the axis of the incident path.

The reflected beam then passes through the chromatic filtering slit which provides spatial filtering of unfocused wavelengths on the surface being inspected, hence an improvement in the sharpness of the image. Downstream of the chromatic filter the reflected beam essentially comprises the focused wavelengths or a narrow range of wavelengths and thus provides a sharp image. The greater the axial chromatic dispersion of the objective, the greater a difference in wavelength gives rise to a greater difference in focal length. The reflected beam then reaches the light intensity sensor. The output from the light intensity sensor is connected to the processing unit.

Figure 14:
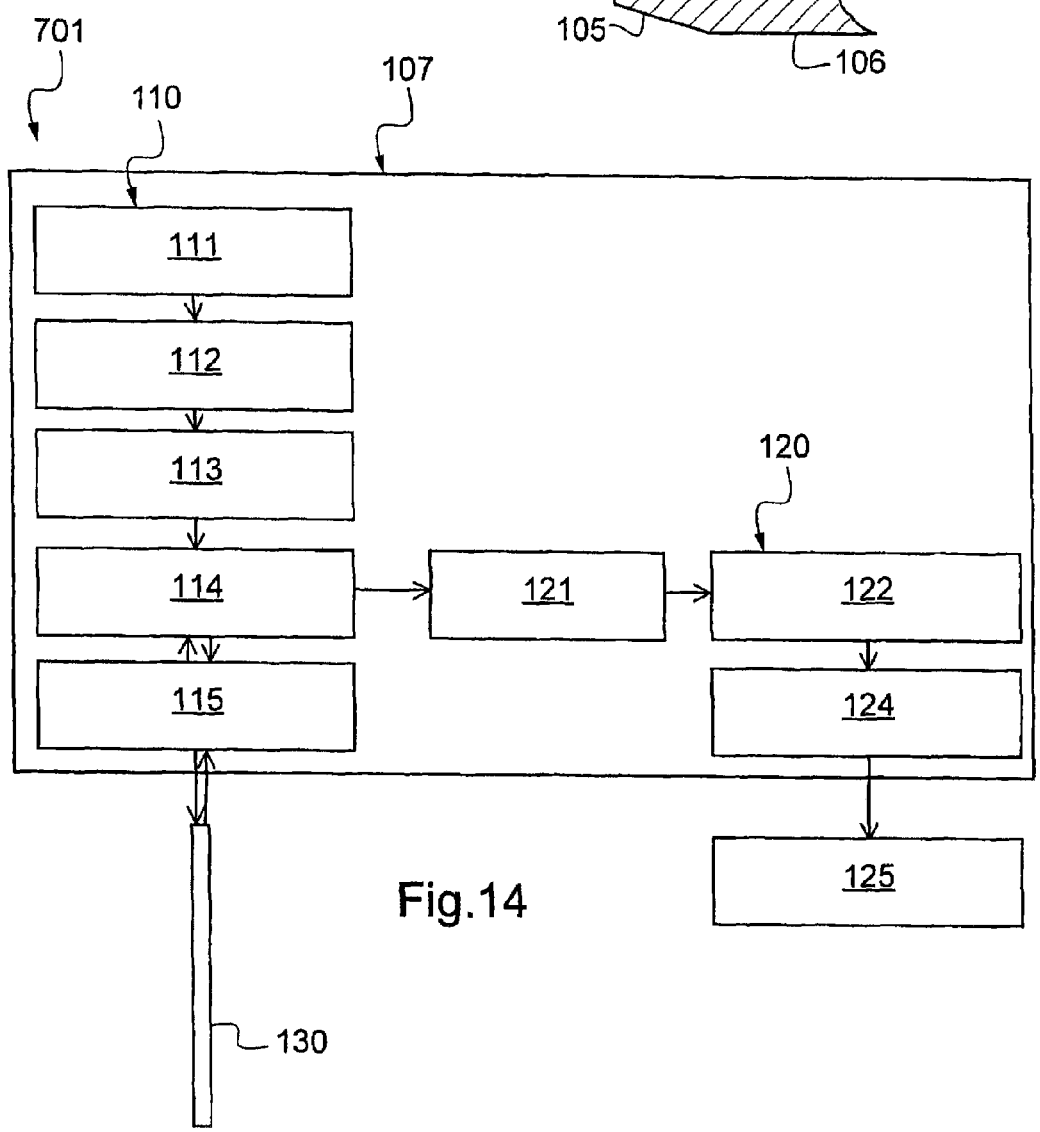
FIG. 14 is a diagrammatical view of an on-board semiconductor wafer inspection device.

As may be seen in FIG. 14, chromatic confocal microscope 107 comprises a lighting path 110 to light up an object 130 under inspection, for example the edge of a semiconductor substrate and an analysis path 120 providing an output signal to a processing and analysis unit 125. Lighting path 110 and analysis path 120 comprise common parts, in particular a semi-reflecting plate 114 and an objective 115.

Lighting path 110 may comprise a broad spectrum source 111 emitting a light beam, a spatial filtering slit 112 receiving this light beam, collimation optics 113 comprising one or more lenses, the semi-reflecting plate 114 mentioned and the objective 115. Semi-reflecting plate 114 receives the incident beam originating from collimation optics 113. The incident beam is directed towards objective 115 when leaving semi-reflecting plate 114. Objective 115 has strong axial chromatic dispersion, in which for example at least one lens is made of a material characterised by chromatic dispersion having an Abbe number of less than 50. By way of example, the Abbe number may be equal to 35. The incident beam reaches the object under inspection 130 after leaving objective 115. Source 111 may comprise a bar of diodes 111a, a homogeniser 111b and an output lens 111c.

Analysis path 120 comprises the objective 115 having strong axial chromatic dispersion, semi-reflecting plate 114 transmitting the reflected beam along an axis different from the inlet axis for the incident beam towards focusing optics that have the opposite function to that of collimation optics 113, complying with the principle of reverse return of the light. Analysis path 120 also comprises a spatial filtering slit 122 located downstream from focusing optics 121. Slit 122 is also located at a distance from the object 130 under inspection which is the same as the distance between spatial filtering slit 112 in lighting path 110 and the object 130 under inspection.

Figure 17:
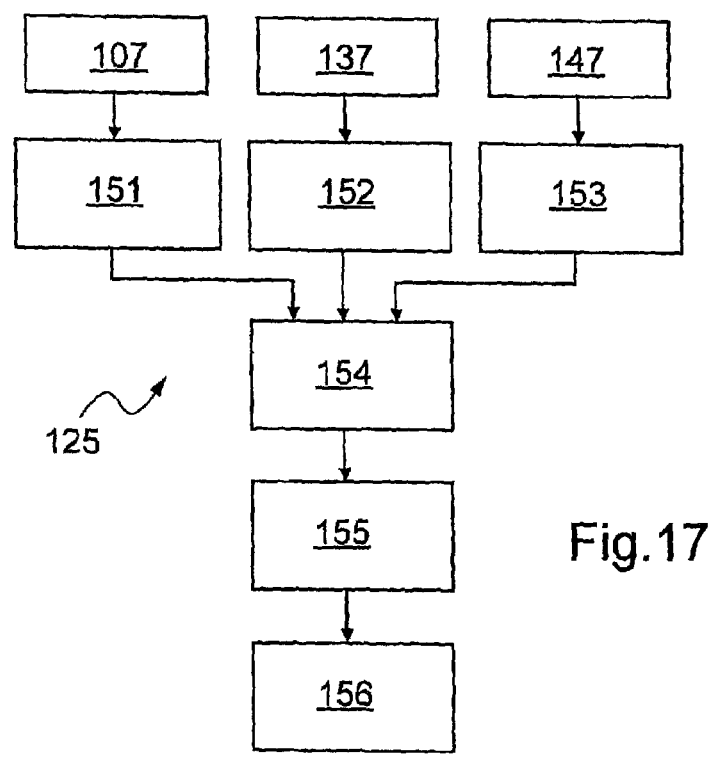
FIG. 17 is a diagrammatical view of a processing unit.

Downstream from spatial filtering slit 122 analysis path 120 comprises a linear sensor 124 located on the path of the reflected beam. Linear sensor 124 may take the form of a set of sensor members arranged on a bar. The sensor members may be of the CCD or CMOS type. The output from microscope 107 downstream from sensor 124 is connected to a processing and analysis unit 125 illustrated in greater detail in FIG. 17. Because spatial filtering slits 112 and 122 are present, and because of the strong axial chromatic dispersion of objective 115, wavelengths which are not focused on the surface of the object 130 under inspection are filtered out because they are spatially offset in relation to the focused wavelength, this offset being greater the greater the axial chromatic dispersion of objective 115. On leaving spatial filtering slit 122 in analysis path 120 the filtered reflected beam comprises a narrow range of wavelengths substantially centred on the focused wavelength, as a result of which the image is very sharp and the filtered reflected beam is representative of defects on the inspected surface of object 130.

In this embodiment microscope 107 measures the reflectivity of the surface of object 130 under inspection. Variations in reflectivity are representative of defects in the inspected surface. From this it is possible to deduce relatively accurate information about the size and nature of defects. In the embodiment illustrated in FIG. 15 analysis path 120 of microscope 107 further comprises a dispersing element 123 located between spatial filtering slit 122 and sensor 124 on the path of the filtered reflected beam. Dispersing element 123 has the function of spatially separating the wavelengths. The spectrum so obtained is projected onto a sensor, and information about the most intense wavelength will then be available, and will provide an image of the optimum focusing distance. Dispersing element 123 may be a diffraction system. Microscope 107 then provides as an output the signal which is representative of the local distance of microscope 107 from the inspected surface of object 130, from which the topography of the inspected surface is deduced. A chromatic information processing unit converts the wavelength into the distance between the edge of the wafer being inspected and the sensor's objective. This embodiment provides a signal which is relatively difficult to process. It proves useful for inspecting semiconductor samples or substrates having defects detected by other means, for example by a microscope 107 according to the embodiment in FIG. 14 which can be incorporated into a production system for semiconductor substrates.

Figure 15:
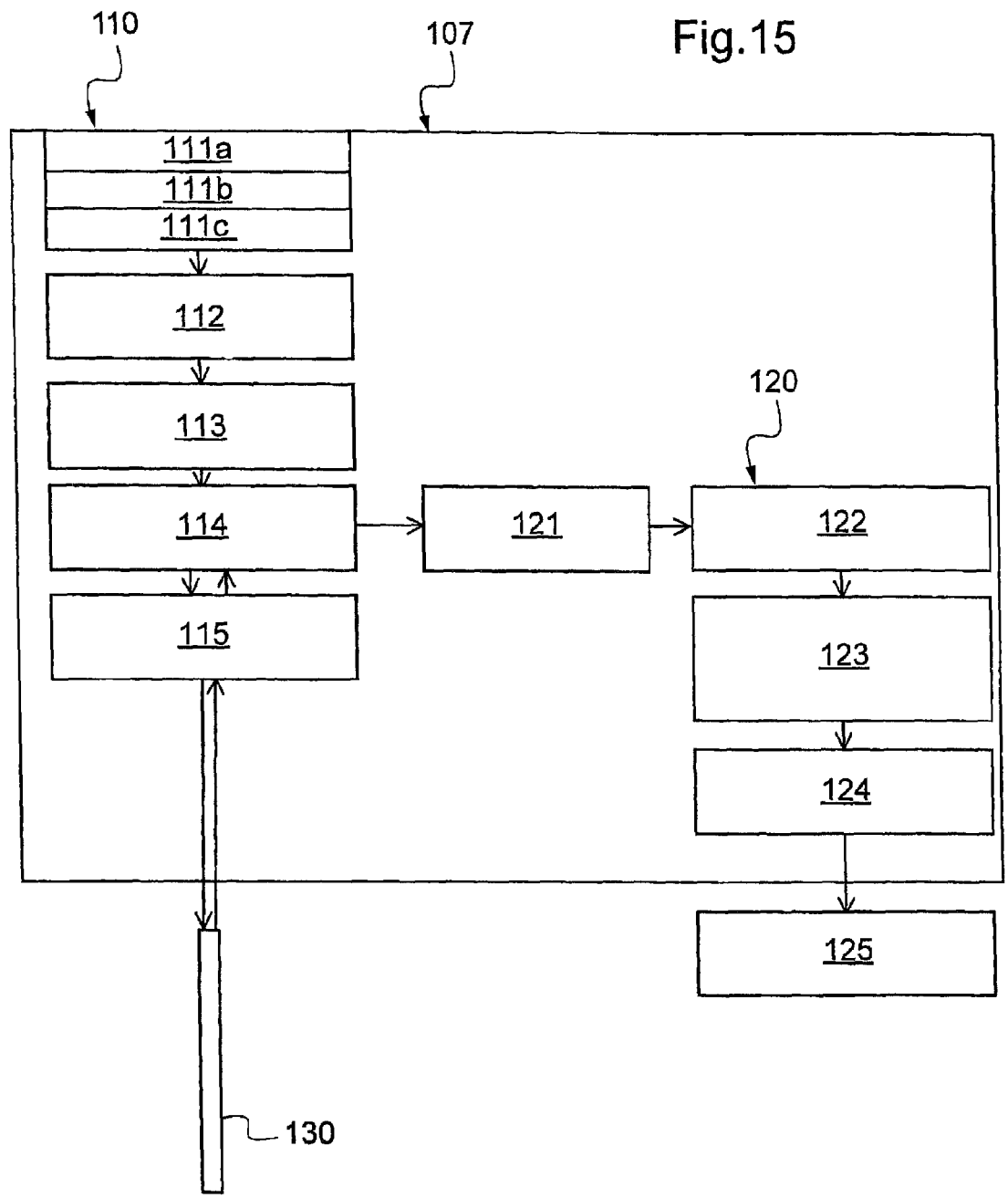
FIG. 15 is a variant of FIG. 14.

A microscope according to the embodiment in FIG. 14 located in the manufacturing system and inspecting a large number or all of the semiconductor substrates manufactured and a microscope according to the embodiment in FIG. 15 to inspect semiconductor substrates having previously detected defects, an inspection which may be 2 to 10 times slower than the previous one, may therefore be provided. The microscope according to the embodiment in FIG. 4 is then located separately from the manufacturing system to receive semiconductor substrates which have been selected because of their defects.

Figure 16:
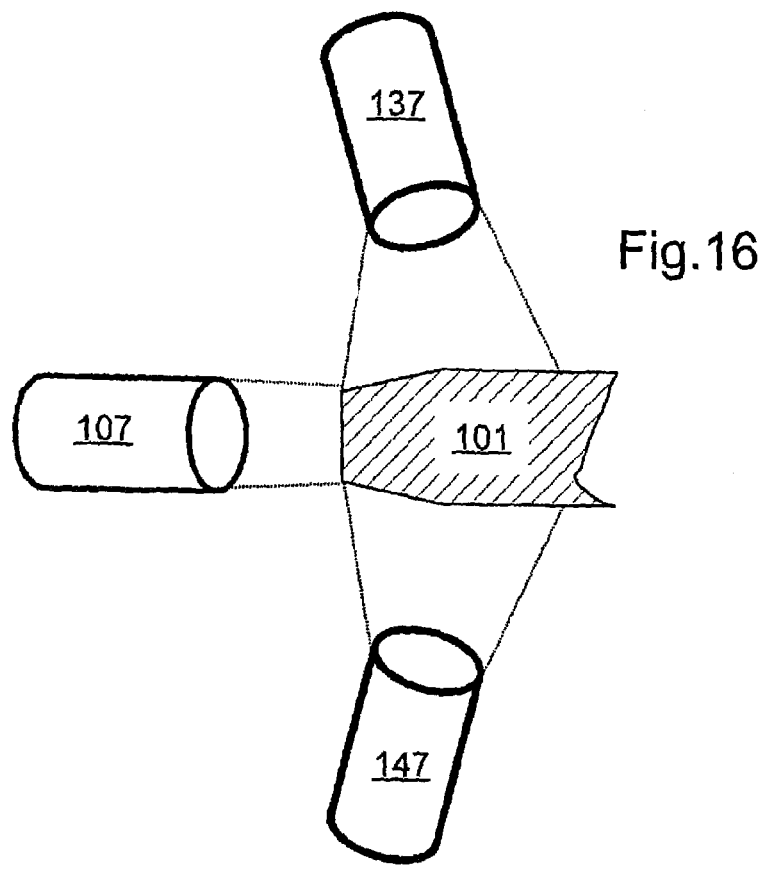
FIG. 16 is a diagrammatical view of an inspection device according to one embodiment.

In the embodiment illustrated in FIG. 16, a plurality of microscopes 107, 137 and 147 are positioned to inspect the edge of the semiconductor substrate 101. Microscopes 17, 137 and 147 may be consistent with the embodiment in FIG. 14. Microscope 107 is positioned opposite side 104 of substrate 101. Microscope 137 is located above substrate 101 to inspect upper bevel 103 and the area close to upper edge 102. Microscope 147 is located beneath substrate 101 to inspect lower bevel 105 and the area close to lower edge 106. The outputs from microscopes 107, 137 and 147 may be connected to a common processing and analysis unit, see FIG. 17.

Processing and analysis unit 125 comprises a plurality of acquisition boards, here three in number. Each acquisition board 151, 152, 153 is connected to the output from a chromatic confocal microscope 107, 137, 147. Processing and analysis unit 125 may also comprise an image reconstruction unit 154 configured to generate an image from the images provided as an output by acquisition boards 151, 152, 153. The image reconstruction unit compares the upper edge of the image of side 104 with the lower extremity of the image of upper bevel 103 and compares the lower edge of the image of side 104 with the upper edge of the image of lower bevel 105. Image reconstruction unit 154 detects any overlap from the result of the comparison and an assembly.

Processing and analysis unit 125 comprises one or more image processing units 155, for example in the form of software, to aid the detection of defects. Image processing units 155 may perform the operations of expansion, erosion, contouring, etc. In addition to this, image processing units 155 may include a library of defects and a comparator to compare suspected defects with known defects listed in the library. Image processing unit 155 is configured to generate a file of results, particularly in the form of an image file, as an output.

In another embodiment, image processing may occur before reconstruction, thus making it possible to have processing which is made easier through having a smaller image size. A combination of results may give rise to a combined result file.

Single Side Topography

Figure 18:
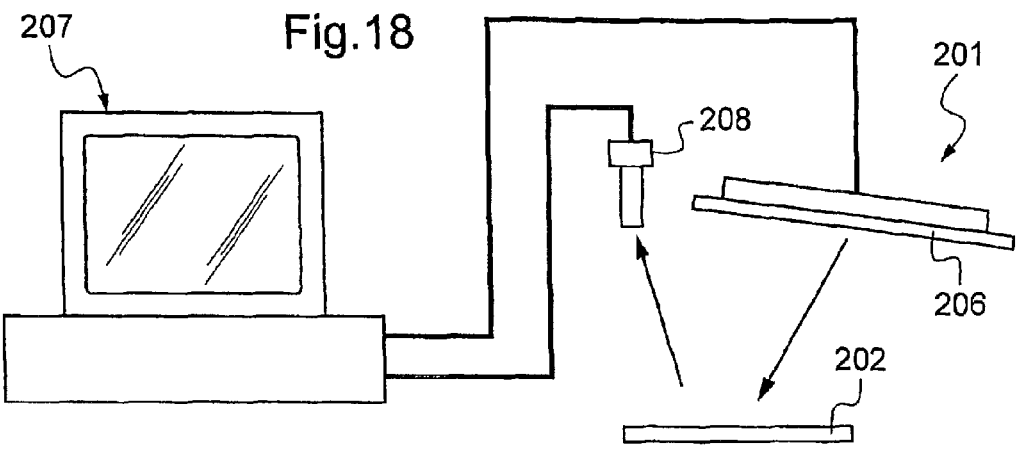
FIGS. 18 to 23 are diagrammatical views illustrating the detection of surface defects by local slope.
Figure 19:
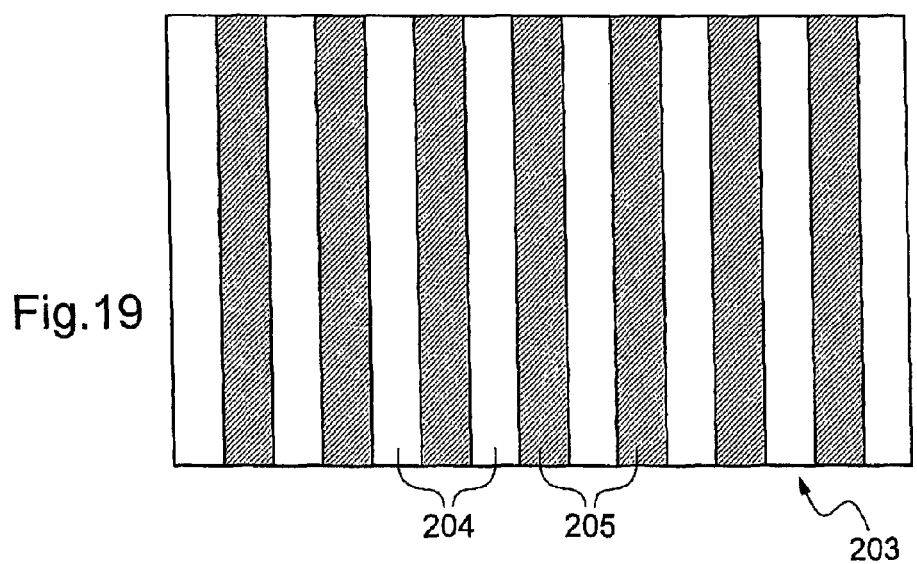

With reference to FIGS. 18 and 19, the device according to the invention comprises means 201 for projecting a pattern 203 comprising an alternation of fringes 204 of continuous light and dark bands 205 onto a substrate 202, the said pattern 203 being illustrated in FIG. 19.

Substrate 202 is positioned on a support, which is not shown in the figures, of an annular type, or of a type having three or four supporting points for a substrate of diameter 300 mm for example.

Light fringes 204 and dark bands 205 are substantially of the same width; however, light fringes 204 and dark bands 205 may have any respective widths.

Projection means 201 comprise a screen 206, such as a plasma screen or an LCD, acronym for "Liquid Crystal Display", screen, for example, positioned above substrate 202 close to the normal to that substrate 202 connected to emission means for a visual signal such as for example a computer 207, and receiving a visual signal comprising a succession of light fringes 204 and dark bands 205.

Preferably an LCD screen of the 50 inch type is used. In fact the uniformity of pixels in LCD screens is more appropriate to the detection of slip lines than that of the pixels in plasma screens. The distance between such screen 206 and a substrate 202 of diameter 300 mm is for example 60 cm.

Screen 206 may also be replaced by a projection screen on which a pattern is projected by a projector. In all circumstances screen 206 is preferably located perpendicular to the optical axis in order to obtain uniform resolution over the entire substrate.

Pattern 203 corresponds to structured light in the plane of screen 206. In the embodiment of pattern 203 illustrated in FIG. 19 the distribution of intensity I(x) perpendicular to the fringes is generally crenelated (FIG. 22), that is to say the intensity varies periodically between 0 and 100%.

Figure 21:
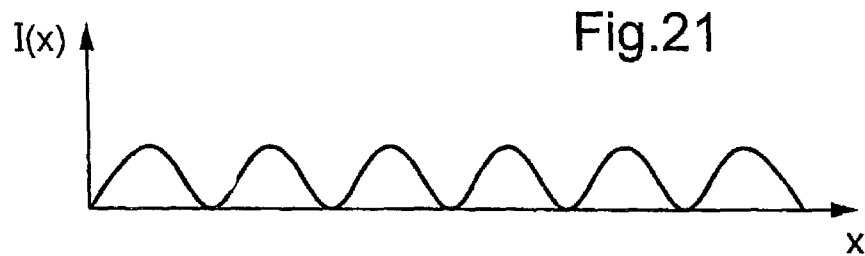

Preferably, pattern 203 comprises parallel fringes in which the distribution of intensity I(x) perpendicular to the fringes is approximately sinusoidal (FIG. 21).

Figure 22:
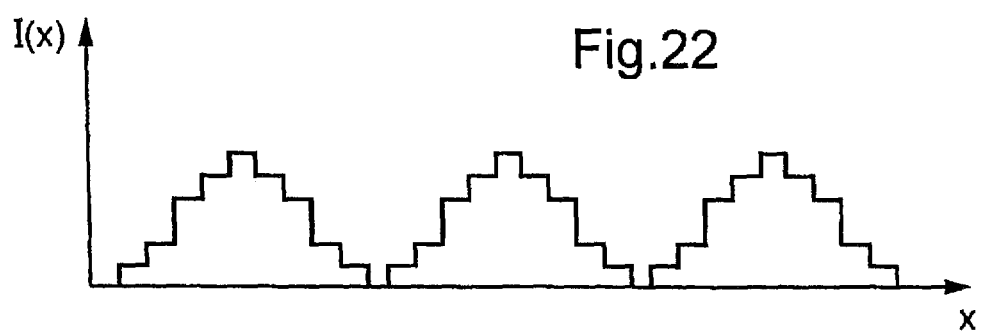
Figure 23:
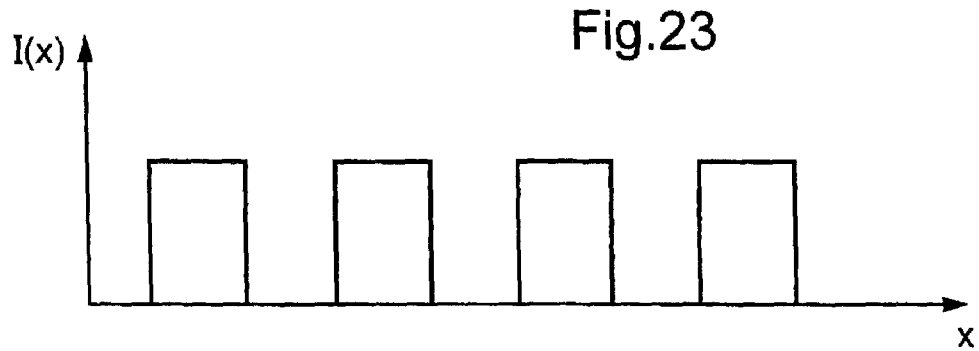

When the period of the sinusoid corresponds to ten or so pixels in a screen 206 the intensity distribution takes a form corresponding to FIG. 22.

In this embodiment very fine fringes 204, corresponding for example to some ten pixels in screen 206, are preferably used. With a screen 206 of 1000 pixels this is equivalent to some hundred light fringes 204 which are reflected by substrate 202.

These projection means 201 may be replaced by any other equivalent projection means capable of projecting a pattern 203 comprising an alternation of fringes 204 of continuous light and dark bands onto the substrate.

These means may for example comprise a continuous sinusoidal light source, i.e. a non-coherent light, and a grid positioned between the light source and the substrate or again a coherent light source comprising two spherical waves which produce sinusoidal fringes through interference between these waves.

The device furthermore comprises means for relative displacement of pattern 203 and substrate 202 in at least one direction. In this particular embodiment the displacement means advantageously comprise the video signal processing algorithm transmitted to screen 206 in such a way as to offset light fringes 204 and dark bands 205 by half a pixel, one pixel or several pixels at regular or irregular intervals of time. In fact the period of the fringes is not necessarily commensurable with the pixels.

Preferably, pattern 203 is displaced by a single pixel. In the case of light fringes 204 having a sinusoidal intensity with a pitch of ten pixels on the screen, ten different images are thus recorded.

Pattern 203 may be displaced stepwise, that is to say by a small displacement, or continuously in one or more directions.

With reference of FIG. 18, the device comprises a sensor 208 with a view in particular to recording the images of fringes 204 reflected by substrate 202 and their displacement. This sensor 208 advantageously comprises a digital camera having a sensor of the CCD type, acronym for "Charge Coupled Device", of 11 million pixels. The camera is adjusted for substrate 202 and not the mirror image of the screen reflected on substrate 202. Such a camera makes it possible to capture an image in 150 ms, and then to transfer the data to a computer in approximately 300 ms. Thus in one second a sufficiently accurate image is acquired to be able to resolve slip lines with the process according to the invention. For a sequence of ten images, data acquisition would therefore last approximately ten seconds. It is thus possible to process two or even three substrates per minute, and thus more than one hundred substrates per hour.

This sensor 208 is connected to a computer 207 which receives information relating to the images reflected by substrate 202 in order to process them.

The higher the resolution of sensor 208, the more the device according to the invention detects small surface defects in the substrate.

Furthermore, in this particular embodiment, screen 206, substrate 202 and sensor 208 are fixed so that the device does not generate any vibration, is not a source of contamination associated with friction between the parts, and does not come out of adjustment. Furthermore, the device has little sensitivity to vibrations.

This information is processed by means to determine the curvature of the surface of substrate 202 from the displacement of fringes 204 in pattern 203.

This method of determining the curvature of the surface of substrate 202 comprises an algorithm recorded in computer 207 capable of calculating the phase offset of fringes 204 of pattern 203 at every point on the surface of substrate 202 from the signal transmitted by sensor 208 and then from this of deducing the radius of curvature at that point on the surface of substrate 202.

The device also comprises means for determining the presence of a surface defect on substrate 202 from variations in the slope of the surface of the substrate. These means for determining the presence of a surface defect comprise a second algorithm recorded in computer 207 capable of calculating the slope values at all points on the surface of the substrate from the phase offsets calculated by the first algorithm.

In a particularly advantageous way, the device comprises means for determining the spatial location of defects on the surface of substrate 202. The means for determining the spatial location of defects comprise an algorithm capable of calculating the abscissa and ordinate in relation to a firm reference point for substrate 202 at each point on the surface of substrate 202 having a radius of curvature greater than or equal to a specific threshold value.

According to a variant embodiment, the means for determining the spatial location of defects may comprise an algorithm capable of calculating the abscissa and ordinate in relation to a fixed reference point on substrate 202 at each point on the surface of substrate 202 which has a local slope distribution which is statistically different from the slope distribution in the rest of substrate 202.

Figure 20:
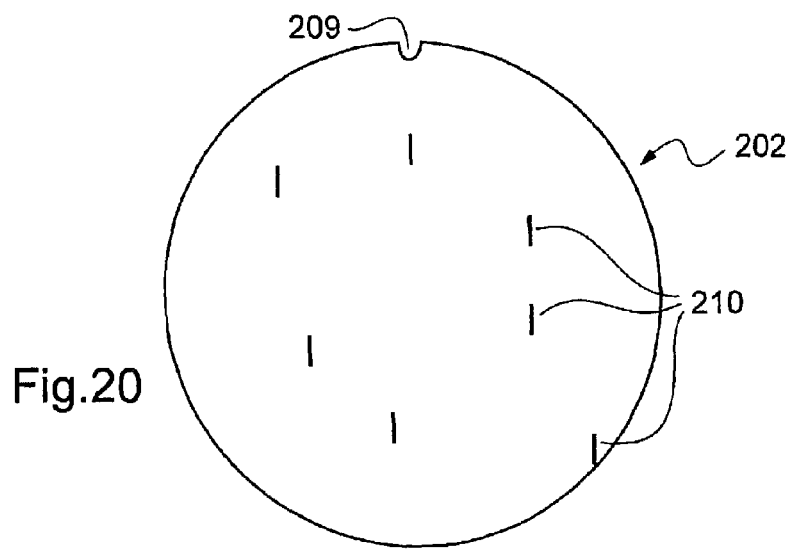

In the embodiment according to the invention, with reference to FIG. 20, substrate 202 comprises a semiconductor substrate of the SOI type (acronym for "Silicon On Insulator") and has the form of a disc having a radial notch 209 on its periphery. This notch 209 forms the reference point for an orthonormal reference in which defects 210 detected on the surface of substrate 202 can be located.

In addition to this, the device comprises means for determining the nature of surface defects comprising an algorithm recorded in computer 207 capable of calculating the amplitude and/or length and/or shape and/or orientation of each surface defect 210 and then comparing these values with those in a database.

Thus the device can be used to detect and distinguish several types of surface defects, in particular micro defects, for example crystal ones, such as slip lines on the periphery of the substrate or support impacts in areas located half-way between the centre and edge of the substrate, the dimensions of which are of the order of several hundred micrometers in the case of length and of the order of a nanometer in the case of depth. The device also makes it possible to detect areas known as "non-transferred" zones (NTZ) appearing in a manufacturing process comprising a stage of transferring a layer and then a stage of detachment using the SmartCut™ process.

In order to reduce dust deposition on substrate 202 and gravitational stresses which are likely to bring about deformation of substrate 202, which may adversely affect the detection of defects 210, substrate 202 is advantageously positioned vertically.

Furthermore the device may advantageously comprise means for generating a flow, preferably a laminar flow, of a fluid in order to minimise contamination of the substrate by dust, substrate 202 preferably extending within the flow or close and parallel to it.

The functioning of the device will now be explained with reference to FIGS. 18 to 21.

Figure 11:
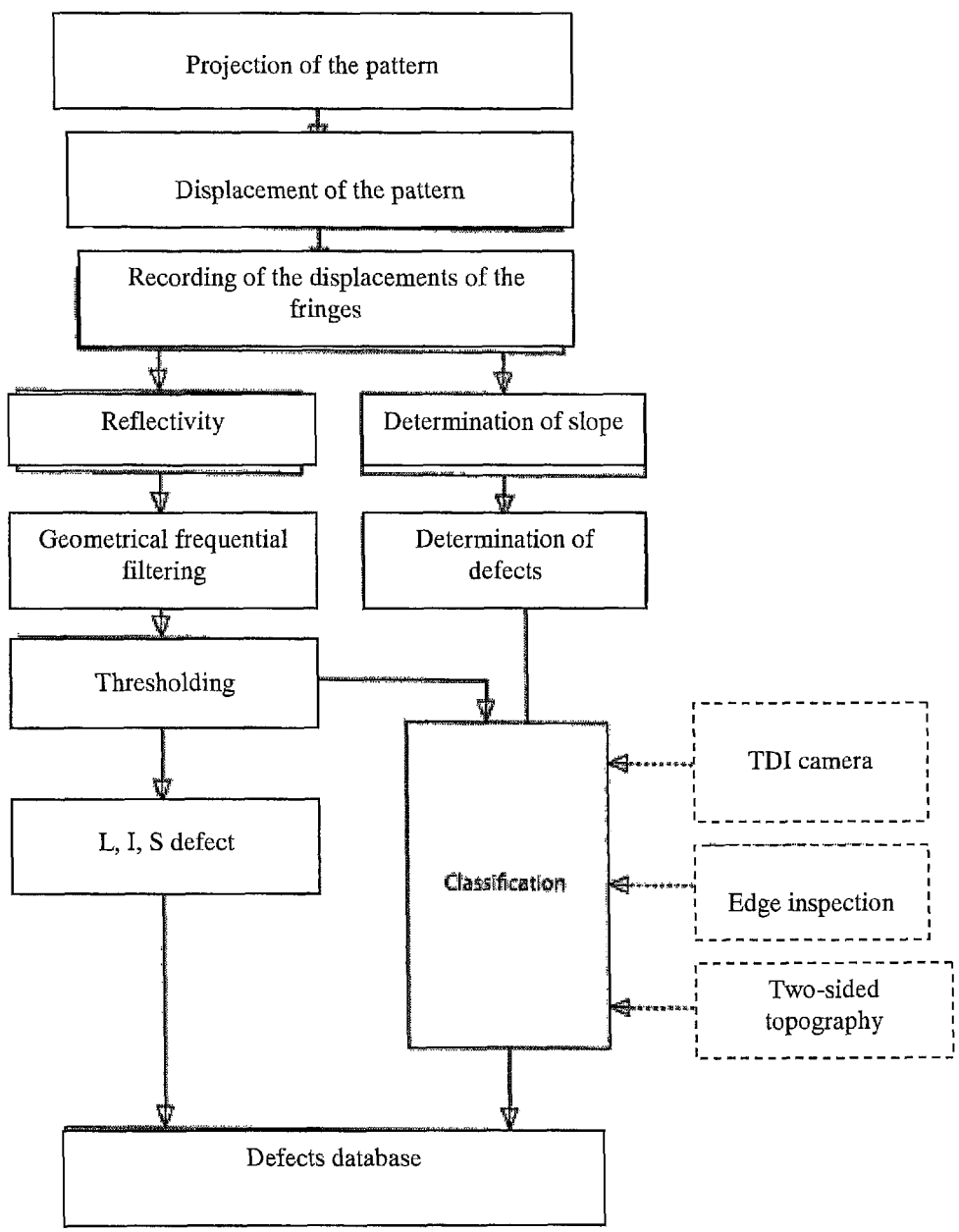
FIG. 11 is a flow chart of stages in the inspection of defects.

A pattern 203, comprising fringes 204 whose light intensity has a sinusoidal distribution over an axis perpendicular to the fringes (FIG. 19) is projected onto substrate 202 in one stage (FIG. 11) in such a way as to generate fringes reflected by the surface of the said substrate.

The intensity of the image affected by the substrate may be written in the form:

$$I = I_0(1 + A_0 \cos(\Phi + x))$$

where $I_0$, $A_0$, $\Phi$ and x are unknowns and represent the mean intensity of the image reflected by its substrate 202, the contrast of fringes 204, a phase angle and a spatial coordinate of a first predetermined direction respectively.

In order to determine these values at each point on the reflected image, in a subsequent stage pattern 203 and substrate 202 are displaced relatively in at least one direction in such a way as to displace the fringes 204 of pattern 203 on substrate 202, and then the displacements of fringes 204 reflected by substrate 202 are recorded in a single stage by means of sensor 208 in order to determine the mean intensity $I_0$, the contrast $A_0$ and phase $\Phi$ of the reflected image at each point in the image. In order to determine the mean intensity $I_0$, the contrast $A_0$ and the phase $\Phi$ of the reflected image at every point in the image it is necessary to acquire a sequence of images. The sequence of images preferably comprises between three and ten images.

Preferably, two sequences of images are required using a pattern 203 comprising parallel fringes 204 extending in the first direction for a first sequence of images, these fringes 204 being displaced at right-angles to the direction of fringes 204, for a first sequence of images, and for a second sequence of images a pattern 203 comprising parallel fringes 204 extending in a direction perpendicular to the direction of fringes 204 of the first sequence of images, these fringes 204 being displaced orthogonally in relation to the direction of fringes 204.

In a particularly advantageous way the sequence and/or sequences of images are acquired by projecting pattern 203 whose fringes 204 extend parallel and/or perpendicular to a principal crystalline axis of the substrate 202. This crystalline axis of the substrate may be physically indicated by a radial notch 209 on the periphery of substrate 202, see FIG. 20. It is thus possible to use several sequences of images, each sequence using a pattern 203 whose fringes 204 are parallel to one of the principal crystalline axes of substrate 202. Preferably a sequence of ten images per axis is recorded. Such an arrangement makes it possible to detect slip lines appearing in the monocrystalline substrate more effectively, these slip lines, which have a wavelength of the order of several hundred microns substantially greater than their width on the atomic scale, being generally aligned with the crystalline axis of substrate 202. Thus a sequence of three images is sufficient for accurate determination of the displacements of fringes 204 and then the presence and location of defects 210 on the substrate, as will be seen below.

The curvature of the surface of substrate 202 is then determined from the displacements of fringes 204 in pattern 203. It will be noted that the curvature at each point on the surface of substrate 202 is calculated by determining the field of local slopes from measurements of the phase of the reflected images from the displacements of fringes 204 in pattern 203 and then deriving the field of local slopes from this.

By local slope is meant the local tangent to the surface and by curvature is meant the local radius of curvature.

In a further stage, at least one surface defect is detected on substrate 202 from variations in the curvature of the surface of substrate 202 as previously calculated.

Advantageously, this stage of detecting at least one defect is subdivided into a first stage to determine the points on the surface of substrate 202 which have a radius of curvature greater than or equal to a specific threshold value and/or a local curvature distribution which is statistically different from the curvature distribution for the rest of substrate 202 and a second stage of determining the spatial location of defects 210 from the variations in slope and/or curvature of the surface of substrate 202.

This special location of defects 210 is determined from a reference point on substrate 202 as described previously. In the case in point, with reference to FIG. 20, substrate 202 comprises a flat disc having a radial notch 209 on its periphery, which forms the reference point.

The process according to the invention may comprise a stage of determining the nature of the surface defects detected, which is obtained by determining the amplitude and/or length and/or shape and/or orientation of each surface defect detected, in particular by measuring reflectivity, followed by geometric frequency filtering and thresholding, then followed by comparing the amplitude and/or length and/or shape and/or orientation of each surface defect detected with a database in order to determine the nature of the surface defects detected in one stage. After thresholding, the classification stage may be carried out. The classification stage may comprise taking into account defect data originating from images captured by time integration, edge inspection or two-sided topographical analysis.

Relative displacement of pattern 203 and 202 takes place in two directions at right angles.

The process according to the invention and the device implementing the process are particularly suitable for the detection of microdefects on monocrystalline substrates, in particular using parallel fringes 204 aligned with the crystalline system of the substrate.

In addition to this, slip lines are thus better indicated than surface scratches on substrate 202, which are of course independent of the latter's crystalline axes.

Preferably the process comprises analysis of the entire surface of substrate 202 to its periphery in a single sequence of images of the "full wafer" type, in particular with a throughput of the order of 100 substrates per hour. Under these conditions the process can achieve high resolution when detecting shallow defects, i.e. defects having a depth of the order of a few nanometers.

The back surface of the substrate may also be analysed. For this purpose the device may comprise a second screen projecting a pattern onto the back face of the substrate and a second sensor, the two sides of the substrate being analysed simultaneously. According to a variant embodiment the device may comprise means for turning over the substrate, such as for example a robotised clamp which seizes the periphery of the substrate, the two surfaces of the substrate being then analysed successively.

Figure 24:
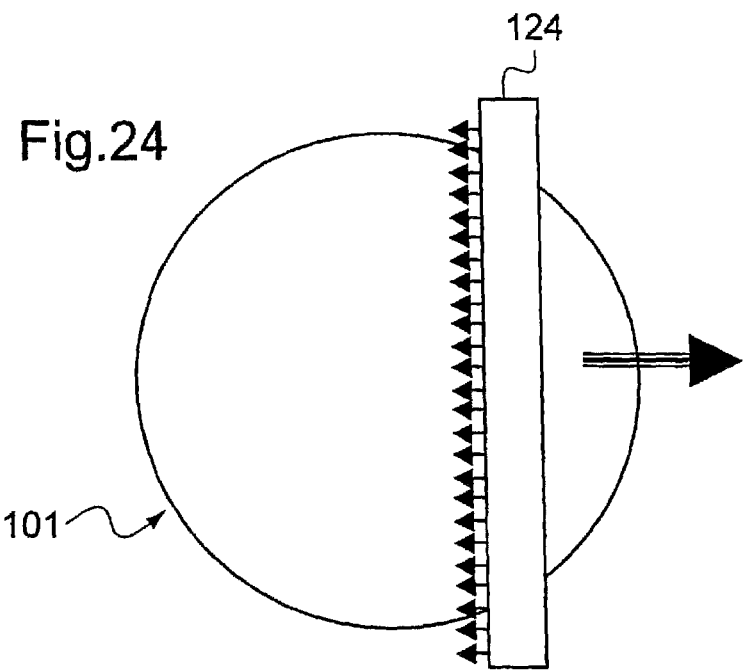
FIGS. 24 and 25 are diagrammatical views illustrating the detection of defects by a linear dark field sensor.
Figure 25:
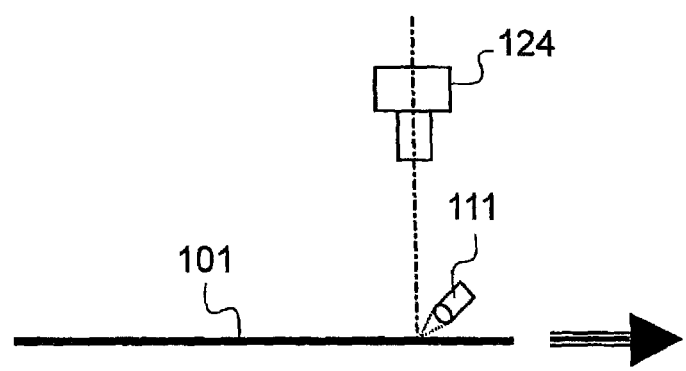

An example of a linear sensor 124 is provided in FIGS. 24 and 25. Linear sensor 124 has the form of a bar. Source 111 comprises light-emitting diodes. Source 111 is directed towards the principal surface of substrate 101. This may be the top surface or the bottom surface. Substrate 101 is moved in the direction of the arrows. The orientation of source 111 and linear sensor 124 is such that linear sensor 124 is adjacent to but outside the beam reflected by the surface of substrate 101. Linear sensor 124 is positioned outside the incident beam to prevent a shadow being formed on the surface of substrate 101. A theoretical perfect surface would generate reflected light whereas an actual surface with defects will generate reflected light and diffracted light. Linear sensor 124 captures the diffracted light corresponding to defects. The dark part of the field of linear sensor 124 corresponds to zones on the surface of substrate 101 where any defects are absent or not detected because of the technological limitations of linear sensor 124.

TABLE 1

| Name of defect | Dark field | Reflectivity | Single-side topography | Front and back topography | Edge inspection | Comments |
|---|---|---|---|---|---|---|
| Non-transferred zone | | | ▓ | | | Lack of material at the SOI, defect during transfer of the thin layer |
| Non-traversing slip line | | | ■ | | | Crystalline dislocation some nm high running for a distance of some hundred microns |
| Traversing slip line | | | | ■ | | |
| Hotspot | ■ | ■ | | | | Defect appearing during the stages of depositing thin layers |
| Tear | ■ | | ■ | | | The same as a non-transferred zone, but at a single location |
| Spot | ■ | | | | | Local inhomogeneity in the refractive index or thickness, having a diameter of several hundred μm to a few mm |
| Marbling associated with variation in thickness | | ■ | | | | Slow variation over surface areas of several cm² |
| Nick | | | | | ■ | Defect on the edge of a wafer |
| Fracture | | ▓ | | | ■ | Initiation of a break in the wafer, starting at the edge, which can propagate over its surface |
| Small particle (a few μm) | ■ | | | | ■ | Present on the surface or edge of the wafer |
| Cleavage lines | ■ | | ■ | | | Start of a break starting anywhere or on the surface |
| Large particle | ■ | ■ | ▓ | | | Present on the surface or edge of the wafer |
| Area of contact with the lifting device | ■ | | ■ | | | Area known as a "lift mark" giving rise to a change in the surface of the substrate in those places where it touched the lifter |
| Narrow scratch | ■ | | | | | |
| Broad scratch | ■ | ■ | | | | |
| Holding finger marks | | | ■ | | | Point of contact between the support and wafer during the stages of heat treatment, giving rise to slip lines and/or local microscratching because of an excessive thermal gradient |

 Signature present at all times

 Signature present under particular conditions

The invention claimed is:

1. A system for inspecting defects in semiconductor wafers comprising:
   a) a first device for detecting surface defects from variations in the slope of a surface of the wafer
   b) a second device for detecting surface defects from variations in the intensity of light reflected by a surface of the wafer at a plurality of points, said second device being configured to calculate the intensity of the light at a plurality of image points to generate an image of the reflected intensities;
   c) a third device for detecting the intensity of the light diffused by the surface of the wafer;
   d) a detection and classification device coupled to an output of each of the first, second and third devices;
   e) a light source common to the first device and the second device, the light source comprising a projection member configured to project a pattern of substantially vertical alternate fringes of continuous light and dark bands onto the surface of the wafer, the projection member comprising a screen having a luminosity of at least 300 cd/cm$^2$;
   f) a controller for displacing the pattern produced by the light source in at least one direction relative to the wafer;
   g) an image capture sensor common to the first, second and third detection devices, the image capture sensor being capable of measuring local light intensity during displacement pattern reflected by the wafer.

2. The system according to claim 1, in which the detection and classification device comprises a classification grid according to which a defect is or is not visible in the image of reflected intensities, and is or is not visible in an image of the variations in the slope of the surface of the wafer.

3. The system according to claim 2, in which the inspection system forms part of a machine comprising an arm for transporting wafers equipped with at least one member supporting wafers, a clamp for seizing the wafers having two arms spaced apart configured to hold the opposite edges of the wafer, the clamp being rotatably mounted on a shaft so that it can turn the wafer between a substantially horizontal position and a substantially vertical position, and at least two inspection systems located on both sides of the wafer in a substantially vertical position, symmetrically with respect to the plane passing through the wafer, the detection and classification mechanism being connected to an output from that inspection system, the classification grid taking into account whether a defect is or is not visible on the two surfaces of the wafer at locations which are close to each other.

4. The system according to claim 2, comprising at least one wafer transport arm fitted with at least one wafer supporting member, the said arm being configured to move at least one plate along a trajectory comprising at least one substantially straight part, the supporting members forming a substantially horizontal support surface in such a way as to hold the wafer substantially horizontal, the device comprising at least one linear time delay integration camera located above the transport arm, the camera having a field covering the straight part of the said trajectory so that the top surface of a semiconductor wafer can be observed by the camera as it moves along a straight part of the trajectory, the detection and classification mechanism being connected to an output from that camera, the classification grid taking into account whether a defect is or is not visible in an image provided by that camera.

5. The system according to claim 4, comprising at least two linear cameras located above the trajectory.

6. The system according to claim 4, comprising at least one linear camera located beneath the trajectory to observe the bottom surface of the wafer, the supporting elements having a first spacing or a first shape on an outward path and a second spacing different from the first spacing or a second shape different from the first shape on the return path, enabling inspection of the entire bottom surface of the wafer, part during the outward path and at least a complementary part during the return path of the wafer along the straight part of the trajectory.

7. The system according to claim 4, comprising two wafer transport arms fitted with supporting members, the supporting members of a first arm having a spacing which is different from or a shape which is different from the supporting members of the second arm, the first arm being configured to provide an outward path for a wafer, the return path being provided by the second arm, thus permitting inspection of the entire bottom surface of the wafer, partly along the outward path and partly along the return path.

8. The system according to claim 4, wherein the camera comprises a rectangular matrix of pixels, being of more than 2000 pixels in length and more than 48 pixels in width, and a summing element to sum the pixels in one width when inspecting a surface of a semiconductor wafer, the camera or cameras being sensitive to ultraviolet radiation, the device further comprising a light source comprising a bar of electroluminescent diodes.

9. The system according to claim 2, comprising a system for inspecting the edge of semiconductor wafers, comprising a chromatic confocal microscope provided with a lighting path and an analysis path, the lighting path comprising a polychromatic light source, a slit and an axially chromatic dispersing objective comprising at least one lens made of a material whose Abbe number is less than 50, and the analysis path comprising the said objective, a chromatic filtering slit and a light intensity sensor in that order, the slit of the lighting path and the slit of the analysis path being located at substantially the same optical distance from the edge of the wafer under inspection, the detection and classification mechanism being connected to an output from the edge inspection system, the classification grid taking into account whether or not a defect is visible on an image provided by the edge inspection system.

10. A process for inspecting defects in semiconductor wafers, comprising:
   measuring the slope of a surface of the wafer using a first device for detecting surface defects;
   measuring variations in the intensity of the light reflected by a surface of the wafer at a plurality of points using a second device for detecting surface defects, wherein the variations of the intensity of the light reflected by the surface of the wafer at a plurality of points is used to generate an image of reflected intensities;
   detecting an intensity of light diffused by the surface of the wafer using a third device for detecting surface defects;
   illuminating the surface of the wafer with a light source common to the first device and the second device, the light source comprising a projection member, wherein the surface of the wafer is illuminated by projecting a pattern of substantially vertical alternate fringes of continuous light and dark bands from the projection member displacing the pattern produced by the light source in at least one direction relative to the wafer;
   measuring local light intensity during displacement of the pattern reflected by the wafer; and;
   classifying surface defects using a detection and classification device coupled to the output of each of the first, second, and third devices.

11. The process according to claim 10, wherein the first device for detecting surface defects and the second device for detecting surface defects are active concurrently during an inspection for another property of the wafer.

12. The process according to claim 10, wherein the wafer rests on at least one supporting member belonging to a transport arm and wherein the method further comprises moving the wafer along a trajectory comprising at least one straight part, and, in the course of the straight part of the trajectory, at least one linear time delay integration camera performs an observation of the top surface of the wafer.

13. The process according to claim 12, in which the inspection is performed before a static inspection.

14. The process according to claim 12, wherein the inspection is performed after a static inspection.

* * * * *

UNITED STATES PATENT AND TRADEMARK OFFICE
CERTIFICATE OF CORRECTION

PATENT NO. : 8,817,249 B2  
APPLICATION NO. : 13/696322  
DATED : August 26, 2014  
INVENTOR(S) : Gastaldo et al.

Page 1 of 1

It is certified that error appears in the above-identified patent and that said Letters Patent is hereby corrected as shown below:

In the Claims:

Claim 10, col. 24, line 60-61, please delete "member displacing" and substitute therefor --member; displacing--.

Signed and Sealed this
Sixth Day of January, 2015

Michelle K. Lee
*Deputy Director of the United States Patent and Trademark Office*